(12) United States Patent
Shinar et al.

(10) Patent No.: US 9,265,445 B2
(45) Date of Patent: Feb. 23, 2016

(54) MONITORING A CONDITION OF A SUBJECT

(71) Applicant: EARLYSENSE LTD., Ramat Gan (IL)

(72) Inventors: Zvika Shinar, Binyamina (IL); Guy Meger, Haifa (IL); Avner Halperin, Ramat Gan (IL)

(73) Assignee: EARLYSENSE LTD., Ramat Gan (IL)

( * ) Notice: Subject to any disclaimer, the term of this patent is extended or adjusted under 35 U.S.C. 154(b) by 0 days.

(21) Appl. No.: 14/810,814

(22) Filed: Jul. 28, 2015

(65) Prior Publication Data

US 2015/0327792 A1 Nov. 19, 2015

Related U.S. Application Data

(60) Continuation of application No. 14/663,835, filed on Mar. 20, 2015, now Pat. No. 9,131,891, which is a continuation-in-part of application No. 14/557,654, filed on Dec. 2, 2014, now Pat. No. 9,026,199, which (Continued)

(51) Int. Cl.
*A61B 5/02* (2006.01)
*A61B 5/04* (2006.01)
*A61B 5/08* (2006.01)
*A61B 5/00* (2006.01)

(52) U.S. Cl.
CPC ............. *A61B 5/0816* (2013.01); *A61B 5/4806* (2013.01); *A61B 5/7275* (2013.01); *A61B 5/7282* (2013.01)

(58) Field of Classification Search
USPC .......................................... 600/300, 509, 511
See application file for complete search history.

(56) References Cited

U.S. PATENT DOCUMENTS

| | | | |
|---|---|---|---|
| 4,686,999 | A | 8/1987 | Snyder |
| 5,902,250 | A | 5/1999 | Verrier |
| 7,077,810 | B2 | 7/2006 | Lange |
| 7,314,451 | B2 | 1/2008 | Halperin |
| 7,351,206 | B2 | 4/2008 | Suzuki |
| 8,376,954 | B2 | 2/2013 | Lange |
| 8,403,865 | B2 | 3/2013 | Halperin |
| 8,491,492 | B2 | 7/2013 | Shinar |

(Continued)

FOREIGN PATENT DOCUMENTS

| | | |
|---|---|---|
| JP | 2004-049838 | 2/2004 |
| JP | 2005-279113 | 10/2005 |

(Continued)

*Primary Examiner* — Nicole F Lavert
(74) *Attorney, Agent, or Firm* — Roach Brown McCarthy & Gruber, P.C.; Kevin D. McCarthy

(57) ABSTRACT

Apparatus for monitoring a subject is described. A sensor detects monitors the subject and generates a signal in response thereto. A control unit analyzes the signal, and in response to the analyzing, identifies a clinical parameter of the subject. The control unit received an indication of a menstrual cycle of the subject. Taking into account the subject's menstrual cycle, the control unit identifies a baseline value of the clinical parameter, compares the identified clinical parameter to the baseline value, and, in response to the comparing, the control unit (a) determines whether a clinical episode is predicted, (b) determines whether a clinical episode is currently occurring, and/or (c) monitors an occurring clinical episode. The control unit generates an output in response thereto. Other applications are also described.

12 Claims, 11 Drawing Sheets

Related U.S. Application Data is a continuation of application No. 14/454,300, filed on Aug. 7, 2014, now Pat. No. 8,942,779, which is a continuation of application No. 14/150,115, filed on Jan. 8, 2014, now Pat. No. 8,840,564, which is a continuation of application No. 13/921,915, filed on Jun. 19, 2013, now Pat. No. 8,679,030, which is a continuation of application No. 13/107,772, filed on May 13, 2011, now Pat. No. 8,491,492, which is a continuation-in-part of application No. 11/782,750, filed on Jul. 25, 2007, now Pat. No. 8,403,865, which is a continuation-in-part of application No. 11/552,872, filed on Oct. 25, 2006, now abandoned, said application No. 14/150,115 is a continuation-in-part of application No. 13/863,293, filed on Apr. 15, 2013, now abandoned, which is a continuation of application No. 11/552,872, filed on Oct. 25, 2006, now abandoned, application No. 14/810,814, which is a continuation-in-part of application No. 14/624,904, filed on Feb. 18, 2015, now Pat. No. 9,131,902, which is a continuation of application No. 14/231,855, filed on Apr. 1, 2014, now Pat. No. 8,992,434, which is a continuation of application No. 14/020,574, filed on Sep. 6, 2013, now Pat. No. 8,731,646, which is a division of application No. 13/750,962, filed on Jan. 25, 2013, now Pat. No. 8,679,034, which is a continuation of application No. 11/782,750, filed on Jul. 25, 2007, now Pat. No. 8,403,865, which is a continuation-in-part of application No. 11/197,786, filed on Aug. 3, 2005, now Pat. No. 7,314,451, said application No. 11/782,750 is a continuation-in-part of application No. 11/446,281, filed on Jun. 2, 2006, now Pat. No. 8,376,954, which is a continuation of application No. 11/048,100, filed on Jan. 31, 2005, now Pat. No. 7,077,810.

(60) Provisional application No. 60/731,934, filed on Nov. 1, 2005, provisional application No. 60/784,799, filed on Mar. 23, 2006, provisional application No. 60/843,672, filed on Sep. 12, 2006, provisional application No. 60/674,382, filed on Apr. 25, 2005, provisional application No. 60/692,105, filed on Jun. 21, 2005, provisional application No. 60/541,779, filed on Feb. 5, 2004.

(56) References Cited

U.S. PATENT DOCUMENTS

| | | | |
|---|---|---|---|
| 8,517,953 | B2 | 8/2013 | Lange |
| 8,585,607 | B2 | 11/2013 | Klap |
| 8,603,010 | B2 | 12/2013 | Lange |
| 8,679,030 | B2 | 3/2014 | Shinar |
| 8,679,034 | B2 | 3/2014 | Halperin |
| 8,731,646 | B2 | 5/2014 | Halperin |
| 8,734,360 | B2 | 5/2014 | Klap |
| 8,821,418 | B2 | 9/2014 | Meger |
| 8,840,564 | B2 | 9/2014 | Pinhas |
| 8,882,684 | B2 | 11/2014 | Halperin |
| 8,942,779 | B2 | 1/2015 | Halperin |
| 8,992,434 | B2 | 3/2015 | Halperin |
| 8,998,830 | B2 | 4/2015 | Halperin |
| 9,026,199 | B2 | 5/2015 | Halperin |
| 2001/0021801 | A1* | 9/2001 | Bardy .................. A61B 5/0002 600/300 |
| 2005/0080349 | A1 | 4/2005 | Okada |
| 2007/0118054 | A1 | 5/2007 | Pinhas |
| 2008/0033304 | A1 | 2/2008 | Dalal |
| 2008/0114260 | A1 | 5/2008 | Lange |
| 2008/0275349 | A1 | 11/2008 | Halperin |
| 2012/0132211 | A1 | 5/2012 | Halperin |
| 2012/0253142 | A1 | 10/2012 | Meger |
| 2013/0245502 | A1 | 9/2013 | Lange |
| 2014/0005502 | A1 | 1/2014 | Klap |
| 2014/0371635 | A1 | 12/2014 | Shinar |
| 2015/0164433 | A1 | 6/2015 | Halperin |
| 2015/0164438 | A1 | 6/2015 | Halperin |
| 2015/0190087 | A1 | 7/2015 | Shinar |

FOREIGN PATENT DOCUMENTS

| | | |
|---|---|---|
| WO | 2007/052108 | 5/2007 |
| WO | 2008/135985 | 11/2008 |
| WO | 2009/138976 | 11/2009 |
| WO | 2015/008285 | 1/2015 |

* cited by examiner

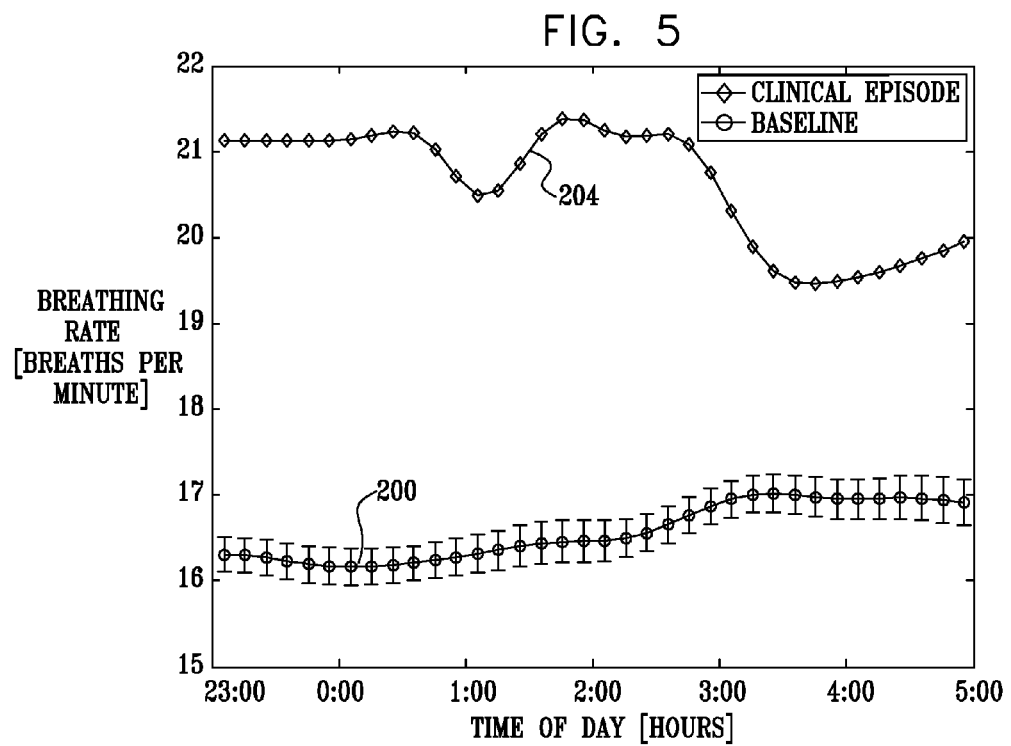
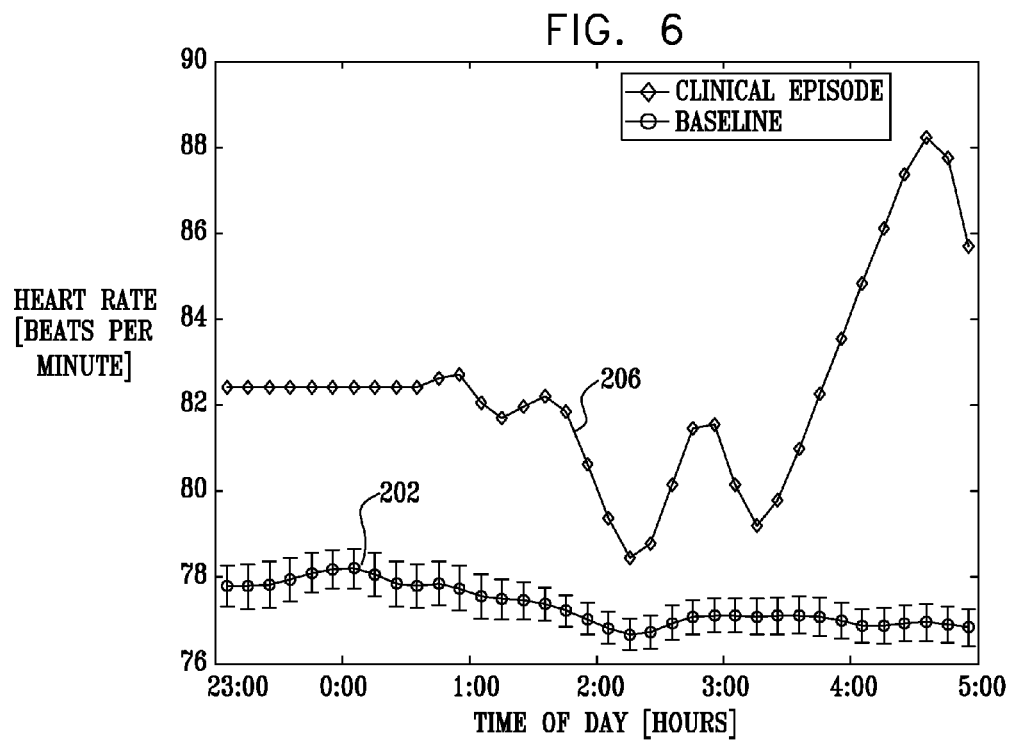

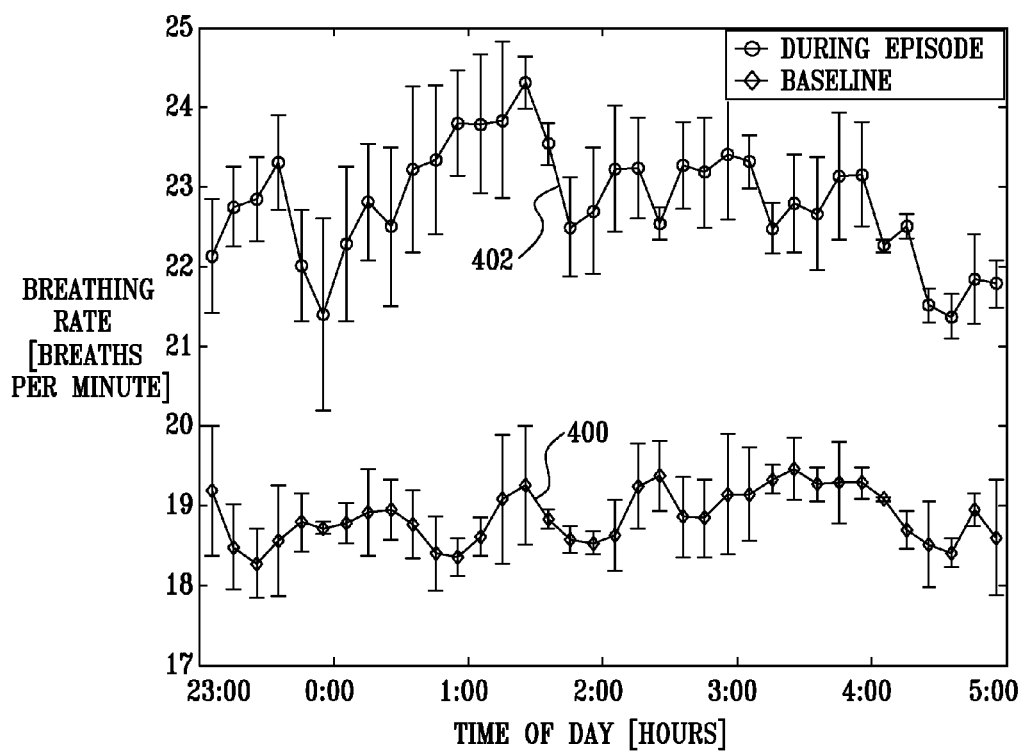

MONITORING A CONDITION OF A SUBJECT

CROSS-REFERENCE TO RELATED APPLICATIONS

The present application is:

(A) a continuation of U.S. patent application Ser. No. 14/663,835 to Shinar (published as US 2015/0190087), filed Mar. 20, 2015, which is a continuation-in-part of U.S. patent application Ser. No. 14/557,654 to Halperin (issued as U.S. Pat. No. 9,026,199), filed Dec. 2, 2014, which is a continuation of U.S. patent application Ser. No. 14/454,300 to Halperin (issued as U.S. Pat. No. 8,942,779), filed Aug. 7, 2014, which is a continuation of U.S. patent application Ser. No. 14/150,115 to Pinhas (issued as U.S. Pat. No. 8,840,564), filed Jan. 8, 2014, which is:

(i) a continuation of U.S. patent application Ser. No. 13/921,915 to Shinar (issued as U.S. Pat. No. 8,679,030), filed Jun. 19, 2013, which is a continuation of U.S. patent application Ser. No. 13/107,772 to Shinar (issued as U.S. Pat. No. 8,491,492), filed May 13, 2011, which:

is a continuation-in-part of U.S. patent application Ser. No. 11/782,750 to Halperin (issued as U.S. Pat. No. 8,403,865), filed Jul. 25, 2007; and is a continuation-in-part of U.S. patent application Ser. No. 11/552,872 to Pinhas (published as US 2007/0118054), filed Oct. 25, 2006, now abandoned, which claims the benefit of:

(a) U.S. Provisional Patent Application 60/731,934 to Halperin, filed Nov. 1, 2005, (b) U.S. Provisional Patent Application 60/784,799 to Halperin filed Mar. 23, 2006, and (c) U.S. Provisional Patent Application 60/843,672 to Halperin, filed Sep. 12, 2006; and (ii) a continuation-in-part of U.S. patent application Ser. No. 13/863,293 to Lange, filed Apr. 15, 2013, published as US 2013/0245502, now abandoned, which is a continuation of U.S. patent application Ser. No. 11/552,872 to Pinhas (published as US 2007/0118054), filed Oct. 25, 2006, now abandoned, which claims the benefit of (a) U.S. Provisional Patent Application 60/731,934 to Halperin, filed Nov. 1, 2005, (b) U.S. Provisional Patent Application 60/784,799 to Halperin filed Mar. 23, 2006, and (c) U.S. Provisional Patent Application 60/843,672 to Halperin, filed Sep. 12, 2006, all of the above applications being incorporated herein by reference; and (B) a continuation-in-part of U.S. patent application Ser. No. 14/624,904 to Halperin, filed Feb. 18, 2015 (published as US 2015/0164433), which is a continuation of U.S. patent application Ser. No. 14/231,855 (issued as U.S. Pat. No. 8,992,434 to Halperin), which is a continuation of U.S. patent application Ser. No. 14/020,574 (issued as U.S. Pat. No. 8,731,646 to Halperin), filed Sep. 6, 2013, which is a divisional of U.S. patent application Ser. No. 13/750,962 (issued as U.S. Pat. No. 8,679,034 to Halperin), filed Jan. 25, 2013, which is a continuation of U.S. patent application Ser. No. 11/782,750 (issued as U.S. Pat. No. 8,403,865 to Halperin), filed Jul. 25, 2007, which is a continuation-in-part of:

(i) U.S. patent application Ser. No. 11/197,786 (issued as U.S. Pat. No. 7,314,451 to Halperin), filed Aug. 3, 2005, which claims the benefit of:

(a) U.S. Provisional Patent Application 60/674,382, filed Apr. 25, 2005, and (b) U.S. Provisional Patent Application 60/692,105, filed Jun. 21, 2005, and (ii) U.S. patent application Ser. No. 11/446,281 (issued as U.S. Pat. No. 8,376,954 to Lange), filed Jun. 2, 2006, which is a continuation of U.S. patent application Ser. No. 11/048,100, filed Jan. 31, 2005, which issued as U.S. Pat. No. 7,077,810, which claims the benefit of U.S. Provisional Patent Application 60/541,779, filed Feb. 5, 2004.

FIELD OF THE INVENTION

Some applications of the present invention relate generally to predicting and monitoring physiological conditions. Specifically, some applications relate to methods and apparatus for monitoring a subject by monitoring the subject's respiration rate and/or the subject's heart rate.

BACKGROUND

Chronic diseases are often expressed by episodic worsening of clinical symptoms. Preventive treatment of chronic diseases reduces the overall dosage of required medication and associated side effects, and lowers mortality and morbidity. Generally, preventive treatment should be initiated or intensified as soon as the earliest clinical symptoms are detected, in order to prevent progression and worsening of the clinical episode and to stop and reverse the pathophysiological process. Therefore, the ability to accurately monitor pre-episodic indicators increases the effectiveness of preventive treatment of chronic diseases.

Many chronic diseases cause systemic changes in vital signs, such as breathing and heartbeat patterns, through a variety of physiological mechanisms. For example, common respiratory disorders, such as asthma, chronic obstructive pulmonary disease (COPD), and cystic fibrosis (CF), are direct modifiers of breathing and/or heartbeat patterns. Other chronic diseases, such as diabetes, epilepsy, and certain heart conditions (e.g., congestive heart failure (CHF)), are also known to modify cardiac and breathing activity. In the case of certain heart conditions, such modifications typically occur because of pathophysiologies related to fluid retention and general cardiovascular insufficiency. Other signs such as coughing and sleep restlessness are also known to be of importance in some clinical situations.

Many chronic diseases induce systemic effects on vital signs. For example, some chronic diseases interfere with normal breathing and cardiac processes during wakefulness and sleep, causing abnormal breathing and heartbeat patterns.

Breathing and heartbeat patterns may be modified via various direct and indirect physiological mechanisms, resulting in abnormal patterns related to the cause of modification. Some respiratory diseases, such as asthma, and some heart conditions, such as CHF, are direct breathing modifiers. Other metabolic abnormalities, such as hypoglycemia and other neurological pathologies affecting autonomic nervous system activity, are indirect breathing modifiers.

Asthma is a chronic disease with no known cure. Substantial alleviation of asthma symptoms is possible via preventive therapy, such as the use of bronchodilators and anti-inflammatory agents. Asthma management is aimed at improving the quality of life of asthma patients.

Monitoring of lung function is viewed as a major factor in determining an appropriate treatment, as well as in patient follow-up. Preferred therapies are often based on aerosol-type medications to minimize systemic side-effects. The efficacy of aerosol type therapy is highly dependent on patient compliance, which is difficult to assess and maintain, further contributing to the importance of lung-function monitoring.

Asthma episodes usually develop over a period of several days, although they may sometimes seem to appear unexpectedly. The gradual onset of the asthmatic episode provides an opportunity to start countermeasures to stop and reverse the inflammatory process. Early treatment at the pre-episode stage may reduce the clinical episode manifestation considerably, and may even prevent the transition from the pre-clinical stage to a clinical episode altogether.

Two techniques are generally used for asthma monitoring. The first technique, spirometry, evaluates lung function using a spirometer, an instrument that measures the volume of air inhaled and exhaled by the lungs. Airflow dynamics are measured during a forceful, coordinated inhalation and exhalation effort by the patient into a mouthpiece connected via a tube to the spirometer. A peak-flow meter is a simpler device that is similar to the spirometer, and is used in a similar manner. The second technique evaluates lung function by measuring nitric-oxide concentration using a dedicated nitric-oxide monitor. The patient breathes into a mouthpiece connected via a tube to the monitor.

Efficient asthma management requires daily monitoring of respiratory function, which is generally impractical, particularly in non-clinical or home environments. Peak-flow meters and nitric-oxide monitors provide a general indication of the status of lung function. However, these monitoring devices do not possess predictive value, and are used as during-episode markers. In addition, peak-flow meters and nitric-oxide monitors require active participation of the patient, which is difficult to obtain from many children and substantially impossible to obtain from infants.

CHF is a condition in which the heart is weakened and unable to circulate blood to meet the body's needs. The subsequent buildup of fluids in the legs, kidneys, and lungs characterizes the condition as congestive. The weakening may be associated with either the left, right, or both sides of the heart, with different etiologies and treatments associated with each type. In most cases, it is the left side of the heart which fails, so that it is unable to efficiently pump blood to the systemic circulation. The ensuing fluid congestion of the lungs results in changes in respiration, including alterations in rate and/or pattern, accompanied by increased difficulty in breathing and tachypnea.

Quantification of such abnormal breathing provides a basis for assessing CHF progression. For example, Cheyne-Stokes Respiration (CSR) is a breathing pattern characterized by rhythmic oscillation of tidal volume with regularly recurring periods of alternating apnea and hyperpnea. While CSR may be observed in a number of different pathologies (e.g., encephalitis, cerebral circulatory disturbances, and lesions of the bulbar center of respiration), it has also been recognized as an independent risk factor for worsening heart failure and reduced survival in patients with CHF. In CHF, CSR is associated with frequent awakening that fragments sleep, and with concomitant sympathetic activation, both of which may worsen CHF. Other abnormal breathing patterns may involve periodic breathing, prolonged expiration or inspiration, or gradual changes in respiration rate usually leading to tachypnea.

SUMMARY OF THE INVENTION

For some applications of the present invention, a subject's respiration rate is monitored for a duration of time of greater than two hours. A parameter of the subject's respiration rate over the time duration, such as the median respiration rate, the mean respiration rate, the maximum respiration rate, and/or a pattern of the respiration rate is determined. The parameter is compared to the same parameter as determined on a previous day during a time period that overlaps with (e.g., is substantially the same as, or partially overlaps with) the time period based upon which the parameter of respiration was determined on the present day. For example, the parameter is compared to the same parameter as determined on a previous day for the same time duration and at the same period (e.g., the same time) of the day. For example, the mean respiration rate over a time duration of three hours, between the times of 8 pm and 11 pm on the present day, may be compared with the mean respiration rate over a time duration of three hours between the times of 8 pm and 11 pm on the previous day. In response thereto, the likelihood of the subject subsequently undergoing an adverse clinical event is determined. Typically, it is determined that the subject is likely to undergo an adverse clinical event by determining that the difference between the parameter of respiration (e.g., the mean respiration rate) of the present day and of the previous day is greater than a threshold amount, e.g., by determining that the parameter of respiration of the present day and that of the previous day are substantially different. Typically, in response to determining that the subject is likely to undergo an adverse clinical event, an alert is generated.

For some applications, the techniques described in the above paragraph with respect to the subject's respiration rate are applied with respect to the subject's heart rate and/or with respect to the subject's respiration rate and the subject's heart rate. For example, it may be determined that the subject is likely to undergo an adverse clinical event by determining that the difference between a parameter of the subject's cardiac cycle (e.g., the mean heart rate over a time duration of greater than two hours at a given period of the day) of the present day and of a previous day is greater than a threshold amount, e.g., by determining that the parameter of the cardiac cycle of the present day and that of the previous day are substantially different. Or, it may be determined that the subject is likely to undergo an adverse clinical event by determining that the difference between a parameter of the subject's cardiac cycle of the present day and of a previous day is greater than a threshold amount, and the difference between a parameter of the subject's respiration of the present day and of a previous day is greater than a threshold amount.

For some applications of the present invention, a subject's motion is monitored for a duration of time of greater than two hours. A parameter of the subject's motion, such as total duration that the subject is in motion, or percentage of time that the subject is in motion, over the time duration is determined. The parameter is compared to the same parameter as determined on a previous day during a time period that overlaps with (e.g., is substantially the same as, or partially overlaps with) the time period based upon which the parameter of respiration was determined on the present day. For example, the parameter is compared to the same parameter as determined on a previous day for the same time duration and at the same period (e.g., the same time) of the day. For example, the total time that the subject is in motion, or percentage of time that the subject is in motion over a time duration of three hours, between the times of 8 pm and 11 pm on the present day, may be compared with the total time that the subject is in motion, or percentage of time that the subject is in motion over a time duration of three hours between the times of 8 pm and 11 pm on the previous day. In response thereto, the likelihood of the subject subsequently undergoing an adverse clinical event is determined. Typically, it is determined that the subject is likely to undergo an adverse clinical event by determining that the difference between the parameter of motion of the present day and of the previous day is greater than a threshold amount, e.g., by determining that the parameter of motion of the present day and that of the previous day are substantially different. Typically, in response to determining that the subject is likely to undergo an adverse clinical event, an alert is generated.

For some applications, the threshold of the cardiac cycle (described hereinabove) is set responsively to a detected respiration rate, and/or responsively to a detected parameter of the subject's motion. Alternatively or additionally, the threshold of the parameter of the subject's respiration (described hereinabove) is set responsively to the detected heart rate, and/or responsively to a detected parameter of the subject's motion. Further alternatively or additionally, the threshold of the parameter of the subject's motion (described hereinabove) is set responsively to the detected heart rate, and/or responsively to the detected respiration rate.

In some embodiments, the present invention includes systems and methods for monitoring uterine contractions, for example, for predicting the onset of preterm labor. Such systems may include a motion acquisition module, a pattern analysis module, and an output module. Aspects of this invention may be used for monitoring uterine contractions and predicting the onset of preterm labor, for example, without viewing or touching the pregnant woman's body, for instance, without obtaining compliance from the woman.

Another embodiment of the invention is a method for detecting uterine contractions in a pregnant woman, the method comprising sensing motion of the woman, for example, without contacting the woman, and generating a signal corresponding to the sensed motion; and analyzing the signal to detect presence of labor contractions. In one aspect, sensing motion of the women comprises sensing motion in the lower abdomen, the pelvis, and the upper abdomen of the women and generating a motion-related signal for the lower abdomen, the pelvis, and the upper abdomen to detect the presence of labor contractions.

Another embodiment of the invention is an apparatus for detecting uterine contractions in a pregnant woman, the apparatus comprising at least one motion sensor adapted to detect motion of the woman, for example, without contacting the woman, and generate at least one signal corresponding to the sensed motion; and a signal analyzer adapted to analyze the at least one signal to detect the presence of labor contractions.

Other embodiments of the invention include methods and systems for monitoring a clinical condition including monitoring clinical parameters during sleep and identifying sleep stages and comparing the clinical parameters in at least one sleep stage to baseline clinical parameters for that sleep stage. The methods and device for identifying sleep stages may include a motion acquisition module, a pattern analysis module and an output module, as described below.

There is therefore provided, in accordance with some applications of the present invention, apparatus, including:

a mechanical sensor configured to detect a physiological signal of a subject without contacting or viewing the subject or clothes that the subject is wearing;

a control unit configured to:

receive the physiological signal from the sensor over a time duration of at least two hours at a given period of at least one first baseline day, determine a physiological parameter of the subject based upon the received physiological signal of the first baseline day;

receive the physiological signal from the sensor over a time duration of at least two hours at a given period of a second day, the period over which the subject's physiological signal is detected on the second day overlapping with the period over which the subject's physiological signal is detected on the first baseline day;

determine a physiological parameter of the subject based upon the received physiological signal of the second day;

compare the physiological parameter based upon the received physiological signal of the second day to the baseline physiological parameter of the subject; and generate an alert in response to the comparison; and an output unit configured to output the alert.

For some applications, the physiological sensor is configured to detect the physiological signal of the subject by detecting a respiration rate of the subject.

For some applications, the physiological sensor is configured to detect the physiological signal of the subject by detecting a heart rate of the subject.

For some applications, the physiological sensor is configured to detect the physiological signal of the subject by detecting a parameter of motion of the subject.

There is further provided, in accordance with some applications of the present invention, apparatus, including:

a sensor configured to detect a respiration signal indicative of a respiration rate of a subject; and a control unit configured to:

receive the detected respiration signal from the sensor over a time duration of at least two hours at a given period of at least one first respiration-rate baseline day;

determine a baseline parameter of the subject's respiration based upon the received respiration signal of the first respiration-rate baseline day;

receive the detected respiration signal from the sensor over a time duration of at least two hours at a given period of a second day, the period over which the subject's respiration is detected on the second day overlapping with the period over which the subject's respiration is detected on the first respiration-rate baseline day;

determine a parameter of the subject's respiration based upon the received respiration signal of the second day;

compare the parameter of the subject's respiration based upon the received respiration signal of the second day to the baseline parameter of the subject's respiration; and generate an alert in response to the comparison; and an output unit configured to output the alert.

For some applications, the control unit is configured to determine the baseline parameter of respiration by determining a baseline respiration pattern based upon the received respiration signal of the first respiration-rate baseline day, and the control unit is configured to determine the parameter of the subject's respiration based upon the received respiration signal of the second day by determining a respiration pattern based upon the received respiration signal of the second day.

For some applications:

the control unit is configured to determine the baseline parameter of respiration by determining a parameter selected from the group consisting of: a mean respiration rate, a maximum respiration rate, and a median respiration rate, based upon the received respiration signal of the first respiration-rate baseline day, and the control unit is configured to determine the parameter of the subject's respiration based upon the received respiration signal of the second day by determining a parameter selected from the group consisting of: a mean respiration rate, a maximum respiration rate, and a median respiration rate, based upon the received respiration signal of the second day.

For some applications, the control unit is configured to:

receive a heart-rate signal from the sensor indicative of a heart rate of the subject over a time duration of at least two hours at a given period of at least one first heart-rate baseline day;

determine a baseline parameter of the subject's cardiac cycle based upon the received heart-rate signal of the first heart-rate baseline day;

receive a heart-rate signal from the sensor indicative of a heart rate of the subject over a time duration of at least two hours at the given period of the second day, the period over which the subject's heart rate is detected on the second day overlapping with the period over which the subject's heart rate is detected on the first heart-rate baseline day;

determine a parameter of the subject's cardiac cycle based upon the received heart-rate signal of the second day; and compare the parameter of the subject's cardiac cycle based upon the received heart-rate signal of the second day to the baseline parameter of the cardiac cycle, and generate the alert by generating the alert in response to (a) the comparison of the parameter of the subject's respiration based upon the received respiration signal of the second day to the baseline parameter of the subject's respiration, and (b) the comparison of the parameter of the subject's cardiac cycle based upon the received heart-rate signal of the second day to the baseline parameter of the subject's cardiac cycle.

For some applications, the control unit is configured to:

receive a motion signal from the sensor indicative of motion of the subject over a time duration of at least two hours at a given period of at least one first motion-parameter baseline day;

determine a baseline parameter of the subject's motion based upon the received motion signal of the first motion-parameter baseline day;

receive a motion signal from the sensor indicative of motion of the subject over a time duration of at least two hours at the given period of the second day, the period over which the subject's motion is detected on the second day overlapping with the period over which the subject's motion is detected on the first motion-parameter baseline day;

determine a parameter of the subject's motion based upon the received motion signal of the second day; and compare the parameter of the subject's motion based upon the received motion signal of the second day to the baseline parameter of motion, and generate the alert by generating the alert in response to (a) the comparison of the parameter of the subject's respiration based upon the received respiration signal of the second day to the baseline parameter of the subject's respiration, and (b) the comparison of the parameter of the subject's motion based upon the received motion signal of the second day to the baseline parameter of the subject's motion.

For some applications, the control unit is configured to compare the parameter of the subject's respiration based upon the received respiration signal of the second day to the baseline parameter of the subject's respiration by determining whether the parameter of the subject's respiration based upon the received respiration signal of the second day differs from the baseline parameter of the subject's respiration by more than a threshold amount.

For some applications, the control unit is configured to:

receive a heart-rate signal from the sensor indicative of a heart rate of the subject; and set the threshold in response to the detected heart-rate signal.

For some applications, the control unit is configured to:

receive a motion signal from the sensor indicative of a motion of the subject; and set the threshold in response to the detected motion signal.

There is additionally provided, in accordance with some applications of the present invention, apparatus, including:

a sensor configured to detect a heart-rate signal indicative of a heart rate of a subject; and a control unit configured to:
  receive the detected heart-rate signal from the sensor over a time duration of at least two hours at a given period of at least one first heart-rate baseline day;
  determine a baseline parameter of the subject's cardiac cycle based upon the received heart-rate signal of the first heart-rate baseline day;
  receive the detected heart-rate signal from the sensor over a time duration of at least two hours at a given period of a second day, the period over which the subject's heart rate is detected on the second day overlapping with the period over which the subject's heart rate is detected on the first heart-rate baseline day;
  determine a parameter of the subject's cardiac cycle based upon the received heart-rate signal of the second day;
  compare the parameter of the subject's cardiac cycle based upon the received heart-rate signal of the second day to the baseline parameter of the subject's cardiac cycle; and
generate an alert in response to the comparison; and
an output unit configured to output the alert.

For some applications, the control unit is configured to:

receive a motion signal from the sensor indicative of motion of the subject over a time duration of at least two hours at a given period of at least one first motion-parameter baseline day;

determine a baseline parameter of the subject's motion based upon the received motion signal of the first motion-parameter baseline day;

receive a motion signal from the sensor indicative of motion of the subject over a time duration of at least two hours at the given period of the second day, the period over which the subject's motion is detected on the second day overlapping with the period over which the subject's motion is detected on the first motion-parameter baseline day;

determine a parameter of the subject's motion based upon the received motion signal of the second day; and compare the parameter of the subject's motion based upon the received motion signal of the second day to the baseline parameter of motion, and generate the alert by generating the alert in response to (a) the comparison of the parameter of the subject's cardiac cycle based upon the received heart-rate signal of the second day to the baseline parameter of the subject's cardiac cycle, and (b) the comparison of the parameter of the subject's motion based upon the received motion signal of the second day to the baseline parameter of the subject's motion.

For some applications, the control unit is configured to compare the parameter of the subject's cardiac cycle based upon the received heart-rate signal of the second day to the baseline parameter of the subject's cardiac cycle by determining whether the parameter of the subject's cardiac cycle based upon the received heart-rate signal of the second day differs from the baseline parameter of the subject's cardiac cycle by more than a threshold amount.

For some applications, the control unit is configured to:

receive a respiration signal from the sensor indicative of a respiration rate of the subject; and set the threshold in response to the detected respiration signal.

For some applications, the control unit is configured to:

receive a motion signal from the sensor indicative of a motion of the subject; and set the threshold in response to the detected motion signal.

There is further provided, in accordance with some applications of the present invention, apparatus, including:

a sensor configured to detect a motion signal indicative of motion of a subject; and a control unit configured to:

receive the detected motion signal from the sensor over a time duration of at least two hours at a given period of at least one first motion-parameter baseline day;

determine a baseline parameter of the subject's motion based upon the received motion signal of the first motion-parameter baseline day;

receive the detected motion signal from the sensor over a time duration of at least two hours at a given period of a second day, the period over which the subject's motion is detected on the second day overlapping with the period over which the subject's motion is detected on the first motion-parameter baseline day;

determine a parameter of the subject's motion based upon the received motion signal of the second day;

compare the parameter of the subject's motion based upon the received motion signal of the second day to the baseline parameter of the subject's motion; and generate an alert in response to the comparison; and an output unit configured to output the alert.

For some applications, the control unit is configured to compare the parameter of the subject's motion based upon the received motion signal of the second day to the baseline parameter of the subject's motion by determining whether the parameter of the subject's motion based upon the received motion signal of the second day differs from the baseline parameter of the subject's motion by more than a threshold amount.

For some applications, the control unit is configured to:

receive a respiration signal from the sensor indicative of a respiration rate of the subject; and set the threshold in response to the detected respiration signal.

For some applications, the control unit is configured to:

receive a heart-rate signal from the sensor indicative of a heart rate of the subject; and set the threshold in response to the detected heart-rate signal.

There is additionally provided, in accordance with some applications of the present invention, a method including:

detecting a respiration rate of a subject over a time duration of at least two hours at a given period of at least one first respiration-rate baseline day;

determining a baseline parameter of the subject's respiration based upon the detected respiration rate for the first respiration-rate baseline day;

detecting a respiration rate of the subject over a time duration of at least two hours at a given period of a second day, the period over which the subject's respiration is detected on the second day overlapping with the period over which the subject's respiration is detected on the first respiration-rate baseline day;

determining a parameter of the subject's respiration based upon the detected respiration rate on the second day;

comparing the parameter of the subject's respiration based upon the detected respiration rate on the second day to the baseline parameter of the subject's respiration; and generating an alert in response to the comparison.

There is further provided, in accordance with some applications of the present invention, a method including:

detecting a heart rate of a subject over a time duration of at least two hours at a given period of at least one first heart-rate baseline day;

determining a baseline parameter of the subject's cardiac cycle based upon the detected heart rate for the first heart-rate baseline day;

detecting a heart rate of the subject over a time duration of at least two hours at a given period of a second day, the period over which the subject's heart rate is detected on the second day overlapping with the period over which the subject's heart rate is detected on the first heart-rate baseline day;

determining a parameter of the subject's cardiac cycle based upon the detected heart rate on the second day;

comparing the parameter of the subject's cardiac cycle based upon the detected heart rate on the second day to the baseline parameter of the subject's cardiac cycle; and generating an alert in response to the comparison.

There is additionally provided, in accordance with some applications of the present invention, a method including:

detecting motion of a subject over a time duration of at least two hours at a given period of at least one first motion-parameter baseline day;

determining a motion parameter of the subject's respiration based upon the detected motion for the first motion-parameter baseline day;

detecting motion of the subject over a time duration of at least two hours at a given period of a second day, the period over which the subject's motion is detected on the second day overlapping with the period over which the subject's motion is detected on the first motion-parameter baseline day;

determining a parameter of the subject's motion based upon the motion detected on the second day;

comparing the parameter of the subject's motion based upon the motion detected on the second day to the baseline parameter of the subject's motion; and generating an alert in response to the comparison.

There is further provided, in accordance with some applications of the present invention, a method including:

detecting a physiological signal of a subject over a time duration of at least two hours at a given period of at least one first baseline day, without contacting or viewing the subject or clothes that the subject is wearing;

determining a physiological parameter of the subject based upon the detected physiological signal for the first baseline day;

detecting the physiological signal of the subject over a time duration of at least two hours at a given period of a second day, the period over which the subject's physiological signal is detected on the second day overlapping with the period over which the physiological signal is detected on the first baseline day;

determining a physiological parameter of the subject based upon the detected physiological signal on the second day;

comparing the physiological parameter based upon the detected physiological signal on the second day to the baseline physiological parameter of the subject; and generating an alert in response to the comparison.

There is therefore provided, in accordance with some applications of the present invention, apparatus for monitoring a clinical condition of a subject, the apparatus including:
a motion sensor configured to monitor the subject, and to generate a signal in response thereto; and
a control unit, configured to:
analyze the signal,
in response to the analyzing, (a) identify a sleep stage of the subject, and (b) identify a clinical parameter of the subject in the identified sleep stage,
monitor the clinical condition, by comparing the clinical parameter to a baseline clinical parameter for the identified sleep stage, and
generate an output in response thereto.

In some applications, the sensor is configured to monitor the subject without contacting or viewing the subject or clothes the subject is wearing.

In some applications, the identified sleep stage is a slow-wave sleep stage, the control unit being configured to identify the clinical parameter of the subject in the slow-wave sleep stage.

In some applications, the identified sleep stage is a rapid-eye-movement (REM) sleep stage, the control unit being configured to identify the clinical parameter of the subject in the REM sleep stage.

In some applications, the clinical parameter is selected from the group consisting of: respiratory rate, and heart rate, the control unit being configured to identify the selected clinical parameter.

In some applications,
the clinical parameter is a left ventricular ejection time (LVET) of the subject,
the control unit being configured to identify the LVET of the subject.

In some applications, the control unit is configured to:
identify an average of a clinical parameter for the identified sleep stage, and
monitor the clinical condition, by comparing the average to the baseline.

In some applications, the control unit is configured to:
identify the average of the clinical parameter for each hour of sleep, and
monitor the clinical condition, by comparing each of the averages to a respective baseline.

In some applications, the control unit is configured to:
analyze the signal at a plurality of times,
in response to the analyzing, (a) ascertain that the sleep stage of the subject at each of the plurality of times is a single given sleep stage, and (b) compute a statistic of the clinical parameter over the plurality of times, and
monitor the clinical condition, by comparing the statistic to the baseline.

In some applications,
the plurality of times is a second plurality of times,
the statistic is a second statistic,
the baseline is a first statistic of the clinical parameter over a first plurality of times that precedes the second plurality of times, and
the control unit is further configured to:
analyze the signal at the first plurality of times, and
in response to the analyzing, (a) ascertain that a sleep stage of the subject at each of the first plurality of times is the given sleep stage, and (b) compute the first statistic.

In some applications,
the baseline is a value of the clinical parameter exhibited during a first sleeping session, and
the control unit is configured to identify the clinical parameter by identifying a value of the clinical parameter exhibited during a second sleeping session that follows the first sleeping session.

In some applications,
the baseline is a value of the clinical parameter exhibited at a first time during a sleeping session, and
the control unit is configured to identify the clinical parameter by identifying a value of the clinical parameter exhibited at a second time during the sleeping session that follows the first time.

In some applications, the control unit is configured to monitor the clinical condition by identifying a likelihood that the subject has fever.

In some applications,
the control unit is further configured to, in response to analyzing the signal, identify that breathing of the subject is labored, and
the control unit is configured to identify a likelihood that the subject has fever in response to: (a) comparing the identified clinical parameter to the baseline, and (b) identifying that breathing of the subject is labored.

In some applications,
the clinical parameter is a left ventricular ejection time (LVET) of the subject,
the control unit being configured to identify a likelihood that the subject has fever in response to comparing the identified LVET to a baseline LVET.

There is further provided, in accordance with some applications of the present invention, apparatus for monitoring a subject, the apparatus including:
a physiological sensor, configured to detect a heart rate of the subject during a sleeping session of the subject, and to generate a sensor signal in response thereto; and
a control unit, configured to:
analyze the sensor signal,
in response to the analyzing, identify a likelihood that the subject ate within a given amount of time before the sleeping session, and
in response to the identifying, generate an output signal indicative that the subject ate within the given amount of time.

In some applications, the physiological sensor is configured to detect the heart rate of the subject without contacting or viewing the subject or clothes the subject is wearing.

In some applications, the control unit is configured to identify the likelihood by determining that the heart rate of the subject is greater than a baseline heart rate.

In some applications, the control unit is configured to identify the likelihood by determining that the heart rate of the subject does not increase over a particular interval by more than a threshold.

There is further provided, in accordance with some applications of the present invention, apparatus for monitoring a subject, the apparatus including:
a motion sensor, configured to detect motion of the subject and to generate a signal in response thereto; and
a control unit, configured to:
analyze the signal,
in response to the analyzing, identify a clinical parameter of the subject,
in response to an environmental change, identify a baseline value for the clinical parameter,
derive a score based on a deviation of the identified clinical parameter from the baseline value,
in response to the score, perform an action selected from the group consisting of: determine whether a clinical episode is predicted, determine whether a clinical episode is currently occurring, and monitor an occurring clinical episode, and generate an output in response thereto.

In some applications, the control unit is configured to identify the baseline value in response to a change in seasons.

There is further provided, in accordance with some applications of the present invention, apparatus for monitoring a subject, the apparatus including:

a motion sensor, configured to detect motion of the subject and to generate a signal in response thereto; and a control unit, configured to:

analyze the signal, in response to the analyzing, identify a clinical parameter of the subject, identify a baseline value for the clinical parameter that corresponds to a day of the week, derive a score based on a deviation of the identified clinical parameter from the baseline value, in response to the score, perform an action selected from the group consisting of: determine whether a clinical episode is predicted, determine whether a clinical episode is currently occurring, and monitor an occurring clinical episode, and generate an output in response thereto.

In some applications, the control unit is configured to identify the baseline value in response to a weekly schedule of the subject.

In some applications, the control unit is configured to identify the baseline value in response to physical activity of the subject generally recurring on a particular day of the week.

In some applications, the control unit is configured to identify a first baseline value corresponding to a weekend day, and a second baseline value, which is different from the first baseline value, corresponding to a weekday.

In some applications, the clinical parameter is a respiration rate of the subject, and the control unit is configured to identify a higher baseline value for a weekend day than for a weekday.

There is further provided, in accordance with some applications of the present invention, apparatus for monitoring a subject, the apparatus including:

a motion sensor, configured to detect motion of the subject and to generate a signal in response thereto; and a control unit, configured to:

analyze the signal, in response to the analyzing, identify a clinical parameter of the subject, in response to a menstrual cycle of the subject, identify a baseline value of the clinical parameter, derive a score based on a deviation of the identified clinical parameter from the baseline value, in response to the score, perform an action selected from the group consisting of: determine whether a clinical episode is predicted, determine whether a clinical episode is currently occurring, and monitor an occurring clinical episode, and generate an output in response thereto.

There is further provided, in accordance with some applications of the present invention, apparatus for monitoring a subject, the apparatus including:

a temperature sensor, configured to detect a room temperature;

a motion sensor, configured to detect motion of the subject and to generate a signal in response thereto; and a control unit, configured to:

analyze the signal, in response to the analyzing, identify a clinical parameter of the subject, in response to the room temperature, identify a baseline value for the clinical parameter, derive a score based on a deviation of the identified clinical parameter from the baseline value, in response to the score, perform an action selected from the group consisting of: determine whether a clinical episode is predicted, determine whether a clinical episode is currently occurring, and monitor an occurring clinical episode, and generate an output in response thereto.

The present invention will be more fully understood from the following detailed description of applications thereof, taken together with the drawings, in which:

BRIEF DESCRIPTION OF THE DRAWINGS

FIGS. 5 and 6 are graphs of exemplary baseline and measured breathing rate and heart rate nighttime patterns, respectively, which are generally similar to FIGS. 6 and 7 of U.S. Pat. No. 7,314,451 to Halperin, which is incorporated herein by reference;

FIG. 7 is a graph of baseline and breathing rate nighttime patterns, respectively, which is the same as FIG. 23 of U.S. Pat. No. 7,314,451 to Halperin;

DETAILED DESCRIPTION OF APPLICATIONS

Figure 1:
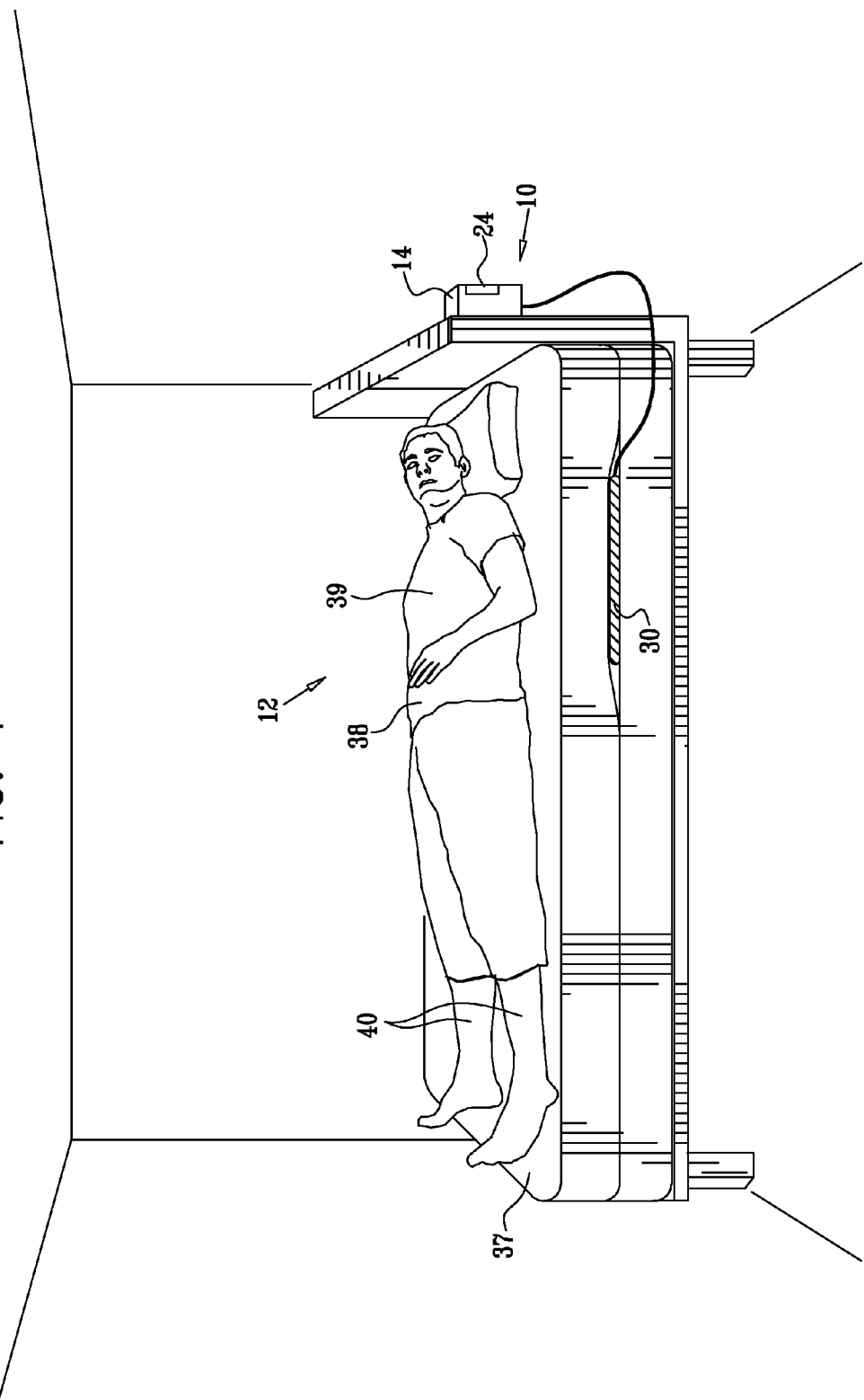
FIG. 1 is a schematic illustration of a system for monitoring a chronic medical condition of a subject, in accordance with some applications of the present invention.

Reference is made to FIG. 1, which is a schematic illustration of a system 10 for monitoring a chronic medical condition of a subject 12, in accordance with some applications of the present invention. System 10 typically comprises a mechanical sensor 30 (e.g., a motion sensor), a control unit 14, and a user interface 24. For some applications, user interface 24 is integrated into control unit 14, as shown in the figure, while for other applications, the user interface and control unit are separate units. For some applications, motion sensor 30 is integrated into control unit 14, in which case user interface 24 is either also integrated into control unit 14 or remote from control unit 14.

Figure 2:
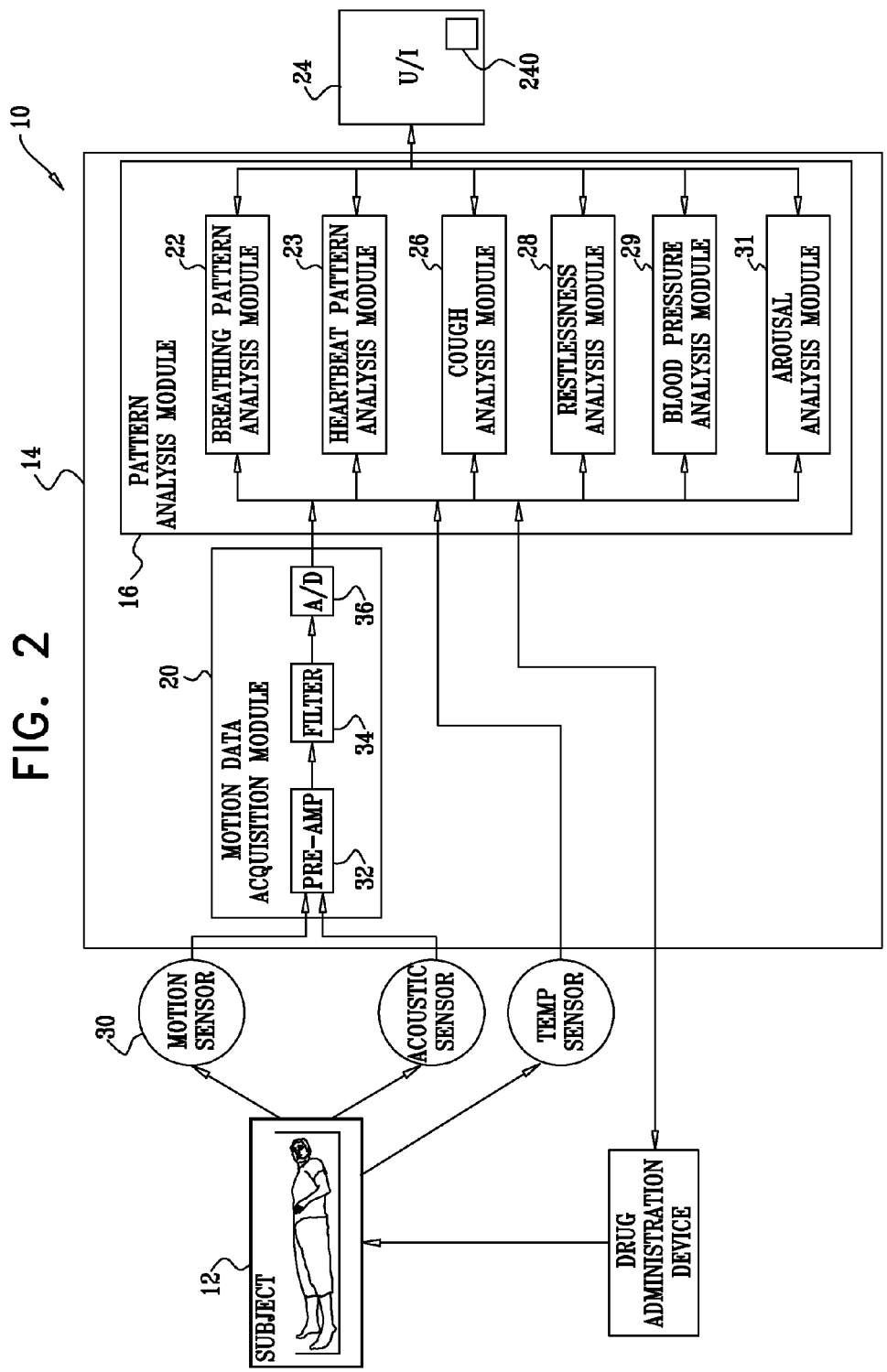
FIG. 2 is a schematic block diagram illustrating components of a control unit of the system of FIG. 1, in accordance with some applications of the present invention.

FIG. 2 is a schematic block diagram illustrating components of control unit 14, in accordance with some applications of the present invention. Control unit 14 typically comprises a motion data acquisition module 20 and a pattern analysis module 16. Pattern analysis module 16 typically comprises one or more of the following modules: a breathing pattern analysis module 22, a heartbeat pattern analysis module 23, a cough analysis module 26, a restlessness analysis module 28, a blood pressure analysis module 29, and an arousal analysis module 31. For some applications, two or more of analysis modules 22, 23, 26, 28, 29, and 31 are packaged in a single housing. For other applications, the modules are packaged separately (for example, so as to enable remote analysis by one or more of the pattern analysis modules of breathing signals acquired locally by data acquisition module 20). For some applications, user interface 24 comprises a dedicated display unit such as an LCD or CRT monitor. Alternatively or additionally, user interface 24 includes a communication line for relaying the raw and/or processed data to a remote site for further analysis and/or interpretation.

For some applications of the present invention, data acquisition module 20 is adapted to non-invasively monitor breathing and heartbeat patterns of subject 12. Breathing pattern analysis module 22 and heartbeat pattern analysis module 23 are adapted to analyze the respective patterns in order to (a) predict an approaching clinical event, such as an asthma attack or heart condition-related lung fluid buildup, and/or (b) monitor the severity and progression of a clinical event as it occurs. For some applications, breathing pattern analysis module 22 and heartbeat pattern analysis module 23 are adapted to analyze the respective patterns in order to determine a likelihood of an approaching adverse clinical event without necessarily identifying the nature of the event. User interface 24 (e.g., via a speaker 240) is adapted to notify subject 12 and/or a healthcare worker of the predicted or occurring event. Prediction of an approaching clinical event facilitates early preventive treatment, which generally reduces the required dosage of medication, and/or lowers mortality and morbidity. When treating asthma, such a reduced dosage generally minimizes the side-effects associated with high dosages typically required to reverse the inflammatory condition once the event has begun.

For some applications of the present invention, pattern analysis module 16 combines parameter data generated from two or more of analysis modules 22, 23, 26, 28, 29, and analyzes the combined data in order to predict and/or monitor a clinical event. For some applications, pattern analysis module 16 derives a score for each parameter based on the parameter's deviation from baseline values (either for the specific patient or based on population averages). Pattern analysis module 16 combines the scores, such as by taking an average, maximum, standard deviation, or other function of the scores. The combined score is compared to one or more threshold values (which may be predetermined) to determine whether an event is predicted, currently occurring, or neither predicted nor occurring, and/or to monitor the severity and progression of an occurring event. For some applications, pattern analysis module 16 learns the criteria and/or functions for combining the individual parameter scores for the specific patient or patient group based on personal history. For example, pattern analysis module 16 may perform such learning by analyzing parameters measured prior to previous clinical events.

Although system 10 may monitor breathing and heartbeat patterns at any time, for some conditions it is generally most effective to monitor such patterns during sleep at night. When the subject is awake, physical and mental activities unrelated to the monitored condition often affect breathing and heartbeat patterns. Such unrelated activities generally have less influence during most night sleep. For some applications, system 10 monitors and records patterns throughout all or a large portion of a night. The resulting data set generally encompasses typical long-term respiratory and heartbeat patterns, and facilitates comprehensive analysis. Additionally, such a large data set enables rejection of segments contaminated with movement or other artifacts, while retaining sufficient data for a statistically significant analysis.

Reference is again made to FIG. 2. Data acquisition module 20 typically comprises circuitry for processing the raw motion signal generated by motion sensor 30, such as at least one pre-amplifier 32, at least one filter 34, and an analog-to-digital (A/D) converter 36. Filter 34 typically comprises a band-pass filter or a low-pass filter, serving as an anti-aliasing filter with a cut-off frequency of less than one half of the sampling rate. The low-passed data is typically digitized at a sampling rate of at least 10 Hz and stored in memory. For example, the anti-aliasing filter cut-off may be set to 5 Hz and the sampling rate set to 40 Hz.

Reference is again made to FIG. 1. Typically, motion sensor 30 detects one or more physiological signal of the subject without contacting or viewing the subject or clothes that the subject is wearing. For some applications of the present invention, motion sensor 30 comprises a pressure gauge (e.g., a piezoelectric sensor) or a strain gauge (e.g., a silicon or other semiconductor strain gauge, or a metallic strain gauge), which is typically adapted to be installed in, on, or under a reclining surface 37 upon which the subject lies, e.g., sleeps, and to sense breathing- and heartbeat-related motion of the subject. "Pressure gauge," as used in the claims, includes, but is not limited to, all of the gauges mentioned in the previous sentence. Typically, reclining surface 37 comprises a mattress, a mattress covering, a sheet, a mattress pad, and/or a mattress cover. For some applications, motion sensor 30 is integrated into reclining surface 37, e.g., into a mattress, and the motion sensor and reclining surface are provided together as an integrated unit. For some applications, motion sensor 30 is adapted to be installed in, on, or under reclining surface 37 in a vicinity of an abdomen 38 or chest 39 of subject 12. Alternatively or additionally, motion sensor 30 is installed in, on, or under reclining surface 37 in a vicinity of a portion of subject 12 anatomically below a waist of the subject, such as in a vicinity of legs 40 of the subject. For some applications, such positioning provides a clearer pulse signal than positioning the sensor in a vicinity of abdomen 38 or chest 39 of the subject. For some applications, motion sensor 30 comprises a fiber optic sensor, for example, as described by Butter and Hocker in Applied Optics 17: 2867-2869 (Sep. 15, 1978).

For some applications, the pressure or strain gauge is encapsulated in a rigid compartment, which typically has a surface area of at least 10 cm^2, and a thickness of less than 5 mm. The gauge output is channeled to an electronic amplifier, such as a charge amplifier typically used with piezoelectric accelerometers and capacitive transducers to condition the extremely high output impedance of the transducer to a low impedance voltage suitable for transmission over long cables. The strain gauge and electronic amplifier translate the mechanical vibrations into electrical signals. Alternatively, the strain gauge output is amplified using a Wheatstone bridge and an amplifier such as Analog Device Module Numbers 3B16, for a minimal bandwidth, or 3B18, for a wider bandwidth (National Instruments Corporation, Austin, Tex., USA).

For some applications of the present invention, motion sensor 30 comprises a grid of multiple pressure or strain gauge sensors, adapted to be installed in, on, or under reclining surface 37. The use of such a grid, rather than a single gauge, may improve breathing and heartbeat signal reception.

Breathing pattern analysis module 22 is adapted to extract breathing patterns from the motion data, and heartbeat pattern analysis module 23 is adapted to extract heartbeat patterns from the motion data. Alternatively or additionally, system 10 comprises another type of sensor, such as an acoustic or air-flow sensor, attached or directed at the subject's face, neck, chest and/or back.

For some applications of the present invention, the subject's respiration rate is monitored for a duration of time of greater than two hours (e.g., greater than three hours, greater than four hours, greater than five hours, or greater than six hours). Breathing pattern analysis module 22 determines a parameter of the subject's respiration rate over the time duration, such as the median respiration rate, the mean respiration rate, the maximum respiration rate, and/or a respiration rate pattern. Module 22 compares the determined parameter to the same parameter as determined on a previous day during a time period that overlaps with the time period based upon which the parameter of respiration was determined on the present day. For example, the parameter is compared to the same parameter as determined on a previous day for the same time duration and at the same period (e.g., the same time) of the day.

For example, the mean respiration rate over a time duration of three hours, between the times of 8 pm and 11 pm on the present day, may be compared with the mean respiration rate over a time duration of three hours between the times of 8 pm and 11 pm on the previous day. In response thereto, the likelihood of the subject subsequently undergoing an adverse clinical event is determined. Typically, it is determined that the subject is likely to undergo an adverse clinical event by determining that the difference between the parameter of respiration (e.g., the mean respiration rate) of the present day and of the previous day is greater than a threshold amount. Typically, in response to determining that the subject is likely to undergo an adverse clinical event, an alert is generated by user interface 24.

For some applications, the period of the day which is compared to the same period of the previous day is a time period, e.g., between 8 pm and 11 pm, as described hereinabove. Alternatively, the period may be defined with respect to the subject's circadian clock, e.g., the period may be the first three hours of the subject's sleep, or from the beginning of the second hour of the subject's sleep to the end of the fifth hour of the subject's sleep.

For some applications, heartbeat pattern analysis module 23 applies generally similar analysis to the subject's heart rate to that described hereinabove with respect to the breathing pattern analysis module 22. For example, module 23 may determine that the subject is likely to undergo an adverse clinical event by determining that the difference between a parameter of the subject's cardiac cycle (e.g., the mean heart rate over a time duration of greater than two hours at a given period of the day) on the present day and that of a previous day is greater than a threshold amount. For some applications, control unit 14 determines that the subject is likely to undergo an adverse clinical event by determining that the difference between a parameter of the subject's cardiac cycle on the present day and that of a previous day is greater than a threshold amount, and the difference between a parameter of the subject's respiration on the present day and that of the previous day is greater than a threshold amount.

As described hereinabove, for some applications, breathing pattern analysis module 22 and heartbeat pattern analysis module 23 are adapted to analyze the respective patterns in order to determine a likelihood of an approaching adverse clinical event without necessarily identifying the nature of the event. Thus, for some applications, in response to determining that the subject is likely to undergo an adverse clinical event, the user interface generates a generic alert signal, in order to indicate to a healthcare professional that an adverse clinical event is imminent.

For some applications, system 10 applies generally similar analysis to a different physiological parameter of the subject to that described hereinabove with respect to the breathing pattern analysis module 22. For example, the system may apply the analysis to a parameter of the subject's motion, such as the total time that the subject is in motion, or percentage of time that the subject is in motion over a given time duration.

Reference is now made to FIGS. 3A-D, which are graphs showing the results of experiments conducted, in accordance with some applications of the present invention. Earlysense Ltd. (Israel) manufactures the EverOn™ system, which is a contact-less piezoelectric sensor placed under a subject's mattress that provides continuous measurement of heart rate and respiration rate of the subject, generally in accordance with the techniques described hereinabove.

A non-interventional study was conducted in two internal medicine departments (Sheba Medical Center and Meir Medical Center, both in Israel). Patients who were admitted due to an acute respiratory condition were enrolled on the study. Patients were monitored by the EverOn™ sensor and followed for major clinical episodes. A major clinical event was defined as death, transfer to ICU, or intubation and mechanical ventilation on the floors. Out of 149 patients included in the study, 96 patients had a length of stay that allowed at least one comparable time window. Ten major clinical events were recorded for these patients. Retrospective analysis of continuous respiratory and heart signal recording was performed. The median respiration rate and heart rate over 6-hour time durations (00-06, 06-12, 12-18, and 18-24) were compared to the median respiration rate and heart rate over a corresponding 6-hour time duration on the previous day. Similarly, the maximum respiration rate and heart rate over 6-hour time durations (00-06, 06-12, 12-18, and 18-24) were compared to the maximum respiration rate and heart rate over a corresponding 6-hour time duration on the previous day. Retrospective receiver operating characteristic (ROC) curve analysis was applied to the results to determine the sensitivity, specificity, positive predictive value, and negative predictive value of using respective thresholds (i.e., thresholds for the difference between median or maximum respiration rate or heart rate and those of the previous day) for determining the likelihood of a subject undergoing (a) any adverse clinical event, i.e., either a major or a moderate clinical event (such as a non-major respiratory event requiring immediate intervention, e.g., bilevel positive airway pressure (BIPAP) or continuous positive airway pressure (CPAP)), or (b) a major clinical event.

Table 1 (shown below) shows the results of the ROC curve analysis of respective combinations of median heart rate and respiration rate thresholds (i.e., thresholds for the difference between median heart rate and respiration rate and those of the previous day) with respect to determining the likelihood of a subject undergoing any adverse clinical event, i.e., either a major or a moderate clinical event.

TABLE 1

| Threshold Heart rate (beats per minute)- Respiration rate (breaths per minute)) | Sensitivity | Specificity | PPV | NPV |
| --- | --- | --- | --- | --- |
| 14-3 | 67 | 82 | 35 | 95 |
| 14-4 | 67 | 82 | 35 | 95 |

TABLE 1-continued

| Threshold Heart rate (beats per minute)-Respiration rate (breaths per minute)) | Sensitivity | Specificity | PPV | NPV |
|---|---|---|---|---|
| 14-5 | 67 | 86 | 40 | 95 |
| 14-6 | 58 | 89 | 44 | 94 |
| 16-3 | 67 | 87 | 42 | 95 |
| 16-4 | 67 | 87 | 42 | 95 |
| 16-5 | 67 | 89 | 47 | 95 |
| 16-6 | 58 | 93 | 54 | 94 |
| 18-3 | 67 | 89 | 47 | 95 |
| 18-4 | 67 | 89 | 47 | 95 |
| 18-5 | 67 | 90 | 50 | 95 |
| 18-6 | 58 | 94 | 58 | 94 |
| 20-3 | 67 | 94 | 62 | 95 |
| 20-4 | 67 | 94 | 62 | 95 |
| 20-5 | 67 | 95 | 67 | 95 |
| 20-6 | 58 | 98 | 78 | 94 |
| 22-3 | 67 | 94 | 62 | 95 |
| 22-4 | 67 | 94 | 62 | 95 |
| 22-5 | 67 | 95 | 67 | 95 |
| 22-6 | 58 | 98 | 78 | 94 |

Table 2 (shown below) shows the results of the ROC curve analysis of respective combinations of median heart rate and respiration rate (i.e., thresholds for the difference between median heart rate and respiration rate and those of the previous day) thresholds with respect to determining the likelihood of a subject undergoing a major clinical event.

TABLE 2

| Threshold (Heart rate (beats per minute)-Respiration rate (breaths per minute)) | Sensitivity | Specificity | PPV | NPV |
|---|---|---|---|---|
| 14-3 | 80 | 83 | 35 | 97 |
| 14-4 | 80 | 83 | 35 | 97 |
| 14-5 | 80 | 86 | 40 | 97 |
| 14-6 | 70 | 90 | 44 | 96 |
| 16-3 | 80 | 87 | 42 | 97 |
| 16-4 | 80 | 87 | 42 | 97 |
| 16-5 | 80 | 90 | 47 | 97 |
| 16-6 | 70 | 93 | 54 | 96 |
| 18-3 | 80 | 90 | 47 | 97 |
| 18-4 | 80 | 90 | 47 | 97 |
| 18-5 | 80 | 91 | 50 | 98 |
| 18-6 | 70 | 94 | 58 | 96 |
| 20-3 | 80 | 94 | 62 | 98 |
| 20-4 | 80 | 94 | 62 | 98 |
| 20-5 | 80 | 95 | 67 | 98 |
| 20-6 | 70 | 98 | 78 | 97 |
| 22-3 | 80 | 94 | 62 | 98 |
| 22-4 | 80 | 94 | 62 | 98 |
| 22-5 | 80 | 95 | 67 | 98 |
| 22-6 | 70 | 98 | 78 | 97 |

It is noted with respect to Tables 1 and 2 that the greatest sum of sensitivity and specificity is for thresholds of 20 or 22 for median heart rate in combination with a threshold of 5 for median respiration rate, both for predicting all adverse clinical events (i.e., major and minor adverse clinical events), and for predicting major clinical events.

Thus, for some applications of the present invention, a subject's heart rate and respiration rate are monitored. The median (or mean, or maximum) heart rate and respiration rate over a time duration of more than two hours and less than eight hours (e.g., greater than three hours, greater than four hours, greater than five hours, or greater than six hours) is determined and is compared to the median (or mean, or maximum) heart rate and respiration rate over a similar time duration at a similar period of the day (e.g., at the same time of day) on at least one previous day (e.g., the previous day). In response to determining (a) that the median (or mean, or maximum) heart rate on the present day differs from that of the previous day by a threshold amount of more than 15 beats per minute, e.g., more than 18 beats per minute, and (b) that the median (or mean, or maximum) respiration rate of the present day differs from that of the previous day by a threshold amount of more than 3 breaths per minute, e.g., more than 4 breaths per minute, then an alert is generated in order to indicate that an adverse clinical event is likely to occur.

Table 3 (shown below) shows the results of the ROC curve analysis of respective maximum heart rate thresholds (i.e., thresholds for the difference between the maximum heart rate and that of the previous day) with respect to determining the likelihood of a subject undergoing a major or a moderate clinical event.

TABLE 3

| Heart rate threshold (beats per minute) | Sensitivity | Specificity | Sum of Sensitivity and Specificity |
|---|---|---|---|
| 0.00 | 1.00 | 0.00 | 1.00 |
| 0.25 | 1.00 | 0.01 | 1.01 |
| 1.00 | 1.00 | 0.02 | 1.02 |
| 3.00 | 0.92 | 0.07 | 0.99 |
| 4.00 | 0.83 | 0.11 | 0.94 |
| 4.50 | 0.83 | 0.17 | 1.00 |
| 5.00 | 0.83 | 0.19 | 1.02 |
| 6.00 | 0.75 | 0.25 | 1.00 |
| 7.00 | 0.75 | 0.32 | 1.07 |
| 8.00 | 0.75 | 0.38 | 1.13 |
| 8.50 | 0.67 | 0.46 | 1.13 |
| 9.00 | 0.67 | 0.48 | 1.14 |
| 10.00 | 0.67 | 0.54 | 1.20 |
| 11.00 | 0.67 | 0.62 | 1.29 |
| 11.50 | 0.67 | 0.70 | 1.37 |
| 12.00 | 0.67 | 0.71 | 1.38 |
| 13.00 | 0.67 | 0.75 | 1.42 |
| 13.50 | 0.67 | 0.79 | 1.45 |
| 14.00 | 0.67 | 0.80 | 1.46 |
| 15.00 | 0.67 | 0.82 | 1.49 |
| 16.00 | 0.67 | 0.85 | 1.51 |
| 17.00 | 0.67 | 0.86 | 1.52 |
| 18.00 | 0.67 | 0.87 | 1.54 |
| 19.00 | 0.67 | 0.89 | 1.56 |
| 20.00 | 0.67 | 0.90 | 1.57 |
| 21.00 | 0.67 | 0.92 | 1.58 |
| 22.00 | 0.67 | 0.93 | 1.60 |
| 22.75 | 0.58 | 0.93 | 1.51 |
| 25.00 | 0.58 | 0.94 | 1.52 |
| 27.00 | 0.50 | 0.95 | 1.45 |
| 28.00 | 0.42 | 0.95 | 1.37 |
| 29.00 | 0.33 | 0.95 | 1.29 |
| 30.75 | 0.17 | 0.95 | 1.12 |
| 32.00 | 0.08 | 0.95 | 1.04 |
| 33.00 | 0.08 | 0.96 | 1.05 |
| 34.00 | 0.08 | 0.98 | 1.06 |
| 53.00 | 0.00 | 0.98 | 0.98 |
| 56.00 | 0.00 | 0.99 | 0.99 |

Figure 3A:
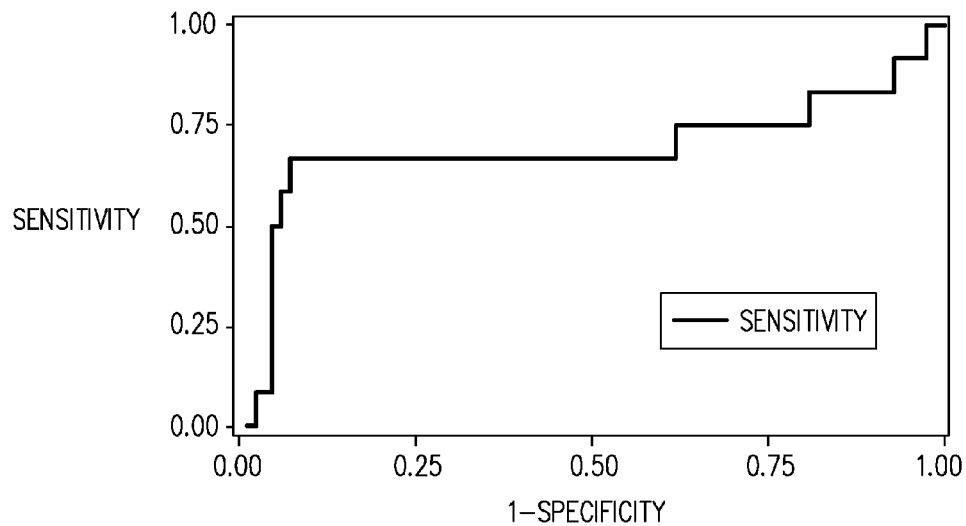
FIGS. 3A-D are graphs showing the results of experiments conducted, in accordance with some applications of the present invention.

It is noted with respect to Table 3 that the greatest sum of sensitivity and specificity is for a heart rate threshold of 22 beats per minute, for predicting major and moderate adverse clinical events. FIG. 3A shows the ROC curve for a heart rate threshold of 22 with respect to predicting a likelihood of either a major or a moderate adverse clinical event. The area under the curve is 0.70 with a standard deviation of 0.11 and a p-value of 0.026.

Table 4 (shown below) shows the results of the ROC curve analysis of respective maximum heart rate thresholds (i.e., thresholds for the difference between the maximum heart rate and that of the previous day) with respect to determining the likelihood of a subject undergoing a major clinical event.

TABLE 4

| Heart rate threshold (beats per minute) | Sensitivity | Specificity | Sum of Sensitivity and Specificity |
|---|---|---|---|
| 0.00 | 1.00 | 0.00 | 1.00 |
| 0.25 | 1.00 | 0.01 | 1.01 |
| 1.00 | 1.00 | 0.02 | 1.02 |
| 3.00 | 1.00 | 0.08 | 1.08 |
| 4.00 | 0.90 | 0.12 | 1.02 |
| 4.50 | 0.90 | 0.17 | 1.07 |
| 5.00 | 0.90 | 0.20 | 1.10 |
| 6.00 | 0.80 | 0.26 | 1.06 |
| 7.00 | 0.80 | 0.33 | 1.13 |
| 8.00 | 0.80 | 0.38 | 1.18 |
| 8.50 | 0.80 | 0.48 | 1.28 |
| 9.00 | 0.80 | 0.49 | 1.29 |
| 10.00 | 0.80 | 0.55 | 1.35 |
| 11.00 | 0.80 | 0.63 | 1.43 |
| 11.50 | 0.80 | 0.71 | 1.51 |
| 12.00 | 0.80 | 0.72 | 1.52 |
| 13.00 | 0.80 | 0.76 | 1.56 |
| 13.50 | 0.80 | 0.79 | 1.59 |
| 14.00 | 0.80 | 0.80 | 1.60 |
| 15.00 | 0.80 | 0.83 | 1.63 |
| 16.00 | 0.80 | 0.85 | 1.65 |
| 17.00 | 0.80 | 0.86 | 1.66 |
| 18.00 | 0.80 | 0.87 | 1.67 |
| 19.00 | 0.80 | 0.90 | 1.70 |
| 20.00 | 0.80 | 0.91 | 1.71 |
| 21.00 | 0.80 | 0.92 | 1.72 |
| 22.00 | 0.80 | 0.93 | 1.73 |
| 22.75 | 0.70 | 0.93 | 1.63 |
| 25.00 | 0.70 | 0.94 | 1.64 |
| 27.00 | 0.60 | 0.95 | 1.55 |
| 28.00 | 0.50 | 0.95 | 1.45 |
| 29.00 | 0.40 | 0.95 | 1.35 |
| 30.75 | 0.20 | 0.95 | 1.15 |
| 32.00 | 0.10 | 0.95 | 1.05 |
| 33.00 | 0.10 | 0.97 | 1.07 |
| 34.00 | 0.10 | 0.98 | 1.08 |
| 53.00 | 0.00 | 0.98 | 0.98 |
| 56.00 | 0.00 | 0.99 | 0.99 |

Figure 3B:
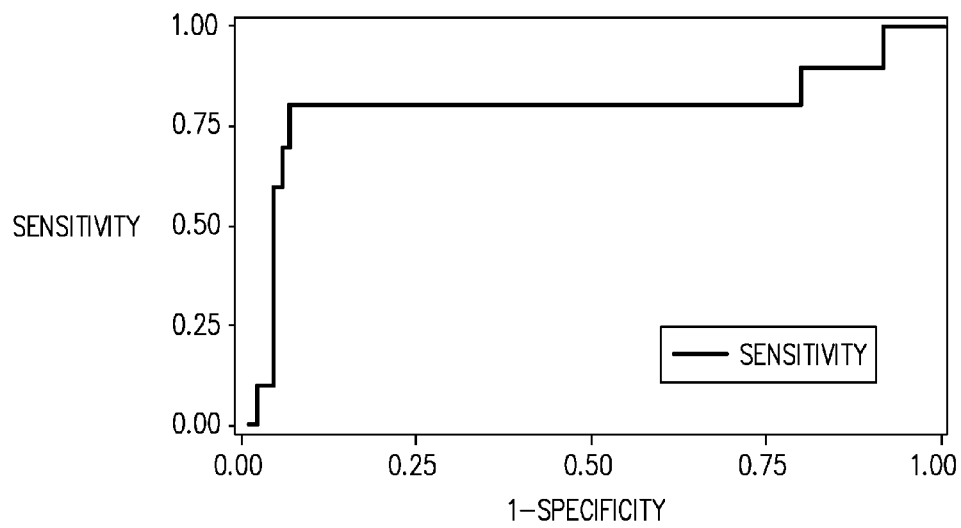

It is noted with respect to Table 4 that the greatest sum of sensitivity and specificity is for a heart rate threshold of 22 beats per minute for predicting major adverse clinical events. FIG. 3B shows the ROC curve for a heart rate threshold of 22 with respect to predicting a likelihood of a major adverse clinical event. The area under the curve is 0.79 with a standard deviation of 0.11 and a p-value of 0.0024.

In general, in accordance with the indications provided by the data in Tables 3 and 4 and in FIGS. 3A and 3B, a subject's heart rate is monitored. The median (or mean, or maximum) heart rate over a time duration of more than two hours and less than eight hours (e.g., greater than three hours, greater than four hours, greater than five hours, or greater than six hours) is determined and is compared to the median (or mean, or maximum) heart rate over a similar time duration at a similar period of the day (e.g., at the same time of day) on at least one previous day (e.g., the previous day). In response to determining (a) that the median (or mean, or maximum) heart rate of the present day differs from that of the previous day by a threshold amount of more than 15 beats per minute (e.g., more than 18 beats per minute, e.g., more than 20 beats per minute), and/or less than 30 beats per minute, then an alert is generated in order to indicate that an adverse clinical event is likely to occur.

Table 5 (shown below) shows the results of the ROC curve analysis of respective maximum respiration rate thresholds (i.e., thresholds for the difference between the maximum respiration rate and that of the previous day), with respect to determining the likelihood of a subject undergoing a major or a moderate clinical event.

TABLE 5

| Respiration rate threshold (breaths per minute) | Sensitivity | Specificity | Sum of Sensitivity and Specificity |
|---|---|---|---|
| 0.00 | 1.00 | 0.00 | 1.00 |
| 0.50 | 1.00 | 0.05 | 1.05 |
| 1.00 | 1.00 | 0.06 | 1.06 |
| 1.50 | 1.00 | 0.24 | 1.24 |
| 2.00 | 1.00 | 0.26 | 1.26 |
| 3.00 | 1.00 | 0.43 | 1.43 |
| 3.50 | 1.00 | 0.58 | 1.58 |
| 4.00 | 1.00 | 0.59 | 1.59 |
| 5.00 | 1.00 | 0.70 | 1.70 |
| 6.00 | 0.69 | 0.76 | 1.46 |
| 6.50 | 0.54 | 0.83 | 1.37 |
| 6.75 | 0.54 | 0.85 | 1.39 |
| 7.00 | 0.46 | 0.85 | 1.31 |
| 7.50 | 0.38 | 0.89 | 1.28 |
| 8.00 | 0.31 | 0.89 | 1.20 |
| 9.00 | 0.23 | 0.92 | 1.15 |
| 10.00 | 0.23 | 0.92 | 1.16 |
| 12.00 | 0.23 | 0.93 | 1.16 |
| 16.00 | 0.23 | 0.97 | 1.20 |
| 18.00 | 0.15 | 0.97 | 1.13 |
| 19.00 | 0.08 | 0.98 | 1.06 |
| 24.00 | 0.00 | 0.98 | 0.98 |
| 35.00 | 0.00 | 0.99 | 0.99 |

Figure 3C:
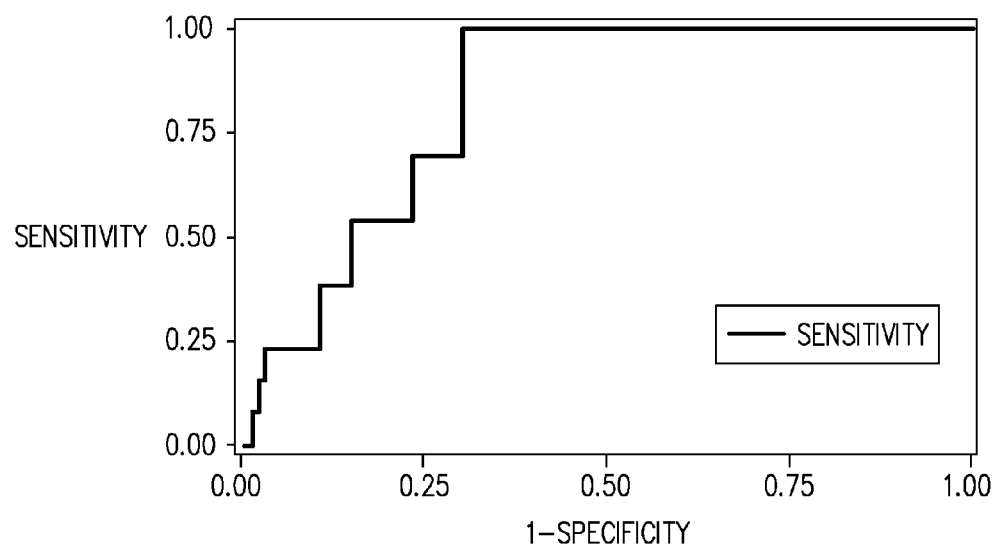

It is noted with respect to Table 5 that the greatest sum of sensitivity and specificity is for a respiration rate threshold of 5 breaths per minute, for predicting major and moderate adverse clinical events. FIG. 3C shows the ROC curve for a respiration rate threshold of 5 with respect to predicting a likelihood of either a major or a moderate adverse clinical event. The area under the curve is 0.84 with a standard deviation of 0.04, and a p-value of 0.000049.

Table 6 (shown below) shows the results of the ROC curve analysis of respective respiration rate thresholds (i.e., thresholds for the difference between the maximum respiration rate and that of the previous day), with respect to determining the likelihood of a subject undergoing a major clinical event.

TABLE 6

| Respiration rate threshold (breaths per minute) | Sensitivity | Specificity | Sum of Sensitivity and Specificity |
|---|---|---|---|
| 0.00 | 1.00 | 0.00 | 1.00 |
| 0.50 | 1.00 | 0.05 | 1.05 |
| 1.00 | 1.00 | 0.06 | 1.06 |
| 1.50 | 1.00 | 0.23 | 1.23 |
| 2.00 | 1.00 | 0.26 | 1.26 |
| 3.00 | 1.00 | 0.42 | 1.42 |
| 3.50 | 1.00 | 0.57 | 1.57 |
| 4.00 | 1.00 | 0.58 | 1.58 |
| 5.00 | 1.00 | 0.69 | 1.69 |
| 6.00 | 0.73 | 0.76 | 1.49 |
| 6.50 | 0.55 | 0.83 | 1.37 |
| 6.75 | 0.55 | 0.84 | 1.39 |
| 7.00 | 0.55 | 0.85 | 1.40 |
| 7.50 | 0.45 | 0.89 | 1.35 |
| 8.00 | 0.36 | 0.89 | 1.26 |
| 9.00 | 0.27 | 0.92 | 1.19 |
| 10.00 | 0.27 | 0.93 | 1.20 |
| 12.00 | 0.27 | 0.93 | 1.21 |
| 16.00 | 0.27 | 0.97 | 1.24 |
| 18.00 | 0.18 | 0.98 | 1.16 |
| 19.00 | 0.09 | 0.98 | 1.07 |
| 24.00 | 0.00 | 0.98 | 0.98 |
| 35.00 | 0.00 | 0.99 | 0.99 |

Figure 3D:
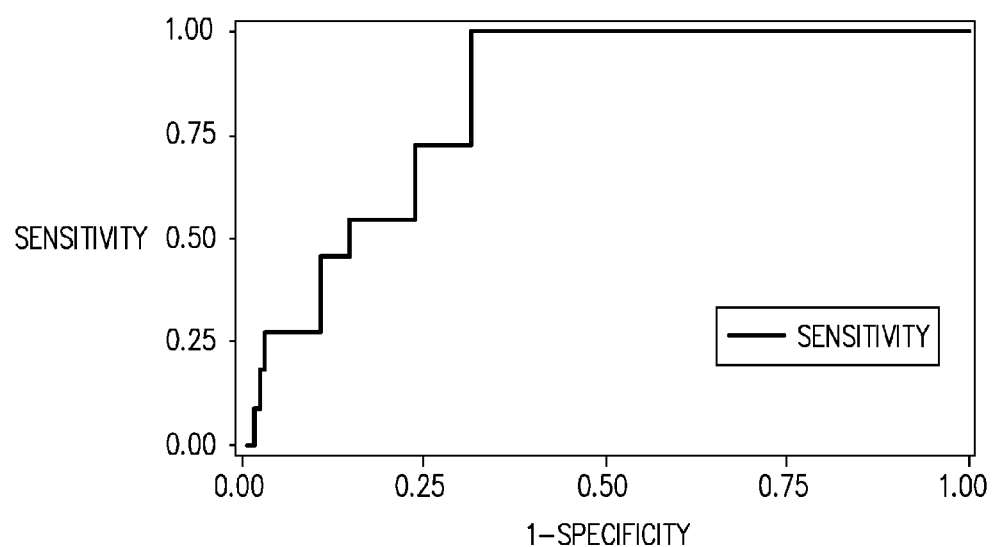

It is noted with respect to Table 6 that the greatest sum of sensitivity and specificity is for a respiration rate threshold of 5 breaths per minute for predicting major adverse clinical events. FIG. 3D shows the ROC curve for a respiration rate threshold of 5 with respect to predicting a likelihood of a major adverse clinical event. The area under the curve is 0.85 with a standard deviation of 0.04, and a p-value of 0.00012.

In general, in accordance with the indications provided by the data in Tables 5 and 6 and in FIGS. 3C and 3D, a subject's respiration rate is monitored. The median (or mean, or maximum) respiration rate over a time duration of more than two hours and less than eight hours (e.g., greater than three hours, greater than four hours, greater than five hours, or greater than six hours) is determined and is compared to the median (or mean, or maximum) respiration rate over a similar time duration at a similar period of the day (e.g., at the same time of day) on at least one previous day (e.g., the previous day). In response to determining (a) that the median (or mean, or maximum) respiration rate of the present day differs from that of the previous day by a threshold amount of more than 3 breaths per minute (e.g., more than 4 breaths per minute), and/or less than 10 breaths per minute (e.g., less than eight, or less than six breaths per minute), then an alert is generated in order to indicate that an adverse clinical event is likely to occur.

For some applications, the techniques described herein are used in combination with the techniques described in one or more of the following references, both of which are incorporated herein by reference:

U.S. Pat. No. 7,077,810 to Lange; and/or
U.S. Pat. No. 7,314,451 to Halperin.

For example, for some applications, as is generally described in U.S. Pat. No. 7,077,810 to Lange, pattern analysis module 22 is configured to predict the onset of an asthma attack or a different clinical event, and/or monitor its severity and progression. Module 22 typically analyzes changes in breathing rate and in breathing rate variability patterns in combination to predict the onset of an asthma attack. Although breathing rate typically slightly increases prior to the onset of an attack, this increase alone is not always a specific marker of the onset of an attack. Therefore, in order to more accurately predict the onset of an attack, and monitor the severity and progression of an attack, module 22 typically additionally analyzes changes in breathing rate variability patterns. For some applications, module 22 compares one or more of the following patterns to respective baseline patterns, and interprets a deviation from baseline as indicative of (a) the onset of an attack, and/or (b) the severity of an attack in progress:

a slow trend breathing rate pattern. Module 22 interprets as indicative of an approaching or progressing attack an increase vs. baseline, for example, for generally healthy subjects, an attenuation of the typical segmented, monotonic decline of breathing rate typically over at least 1 hour, e.g., over at least 2, 3, or 4 hours, or the transformation of this decline into an increasing breathing rate pattern, depending on the severity of the attack;

a breathing rate variability pattern. Module 22 interprets as indicative of an approaching or progressing attack a decrease in breathing rate variability. Such a decrease generally occurs as the onset of an episode approaches, and intensifies with the progression of shortness of breath during an attack;

a breathing duty-cycle pattern. Module 22 interprets a substantial increase in the breathing duty-cycle as indicative of an approaching or progressing attack. Breathing duty-cycle patterns include, but are not limited to, inspirium time/total breath cycle time, expirium time/total breath cycle time, and (inspirium+expirium time)/total breath cycle time; and interruptions in breathing pattern such as caused by coughs, sleep disturbances, or waking. Module 22 quantifies these events, and determines their relevance to prediction of potential asthma attacks.

Figure 4:
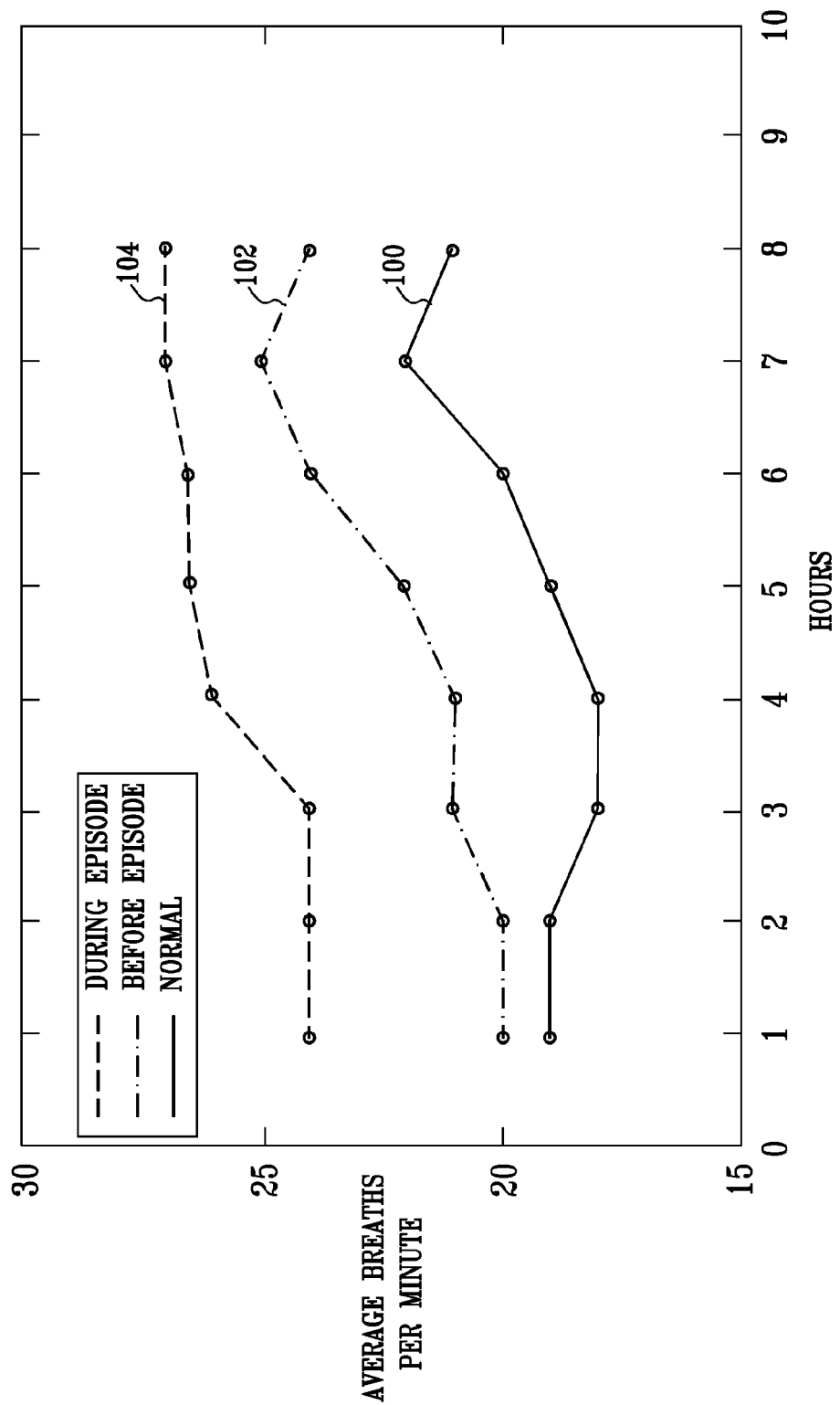
FIG. 4 is a graph illustrating breathing rate patterns of a chronic asthma patient, which is the same as FIG. 4 of U.S. Pat. No. 7,077,810 to Lange, which is incorporated herein by reference.

Reference is made to FIG. 4, which is a graph illustrating breathing rate patterns of a chronic asthma patient, and which is the same as FIG. 4 of U.S. Pat. No. 7,077,810 to Lange. Breathing of the asthma patient was monitored during sleep on several nights. The patient's breathing rate was averaged for each hour of sleep (excluding periods of rapid eye movement (REM) sleep). During the first approximately two months that the patient was monitored, the patient did not experience any episodes of asthma. A line 100 is representative of a typical slow trend breathing pattern recorded during this non-episodic period, and thus represents a baseline slow trend breathing rate pattern for this patient. It should be noted that, unlike the monotonic decline in breathing rate typically observed in non-asthmatic patients, the baseline breathing rate pattern of the chronically asthmatic patient of the experiment reflects an initial decline in breathing rate during the first few hours of sleep, followed by a gradual increase in breathing rate throughout most of the rest of the night.

Lines 102 and 104 were recorded on two successive nights at the conclusion of the approximately two-month period, line 102 on the first of these two nights, and line 104 on the second of these two nights. The patient experienced an episode of asthma during the second of these nights. Lines 102 and 104 thus represent a pre-episodic slow trend breathing rate pattern and an episodic slow trend breathing rate pattern, respectively. As can be seen in the graph, the patient's breathing rate was substantially elevated vs. baseline during all hours of the pre-episodic night, and even further elevated vs. baseline during the episodic night.

Using techniques described herein, the pattern of line 102 is compared with the baseline pattern of line 100, in order to predict that the patient may experience an asthmatic episode. The pattern of line 104 is compared with the baseline pattern of line 100 in order to assess a progression of the asthmatic episode.

In accordance with the data shown in FIG. 4, for some applications, a subject's respiration is detected on first and second days over similar time durations and at similar time periods (e.g., during the first two, three four, five, or six hours of the subject's sleep). A parameter of the subject's respiration based upon the detected respiration rate on the second day is compared with that of the first day. An alert is generated in response to the comparison indicating that an adverse clinical event is approaching, e.g., in response to determining that the difference between the median, the mean, and/or the maximum respiration rate on the second day and that of the first day exceeds a threshold.

For some applications, techniques as described in U.S. Pat. No. 7,314,451 to Halperin are used in conjunction with the techniques described herein. For example, for some applications, system 10 monitors and records patterns throughout all or a large portion of a night. The resulting data set generally encompasses typical long-term respiratory and heartbeat patterns, and facilitates comprehensive analysis. Additionally, such a large data set enables rejection of segments contaminated with movement or other artifacts, while retaining sufficient data for a statistically significant analysis.

Although breathing rate typically slightly increases prior to the onset of an asthma attack (or a different adverse clinical event), this increase alone is not always a specific marker of the onset of an attack. Therefore, in order to more accurately predict the onset of an attack, and monitor the severity and progression of an attack, in an embodiment of the present invention, breathing pattern analysis module 22 additionally analyzes changes in breathing rate variability patterns. For some applications, module 22 compares one or more of the following patterns to respective baseline patterns, and interprets a deviation from baseline as indicative of (a) the onset of an attack, and/or (b) the severity of an attack in progress:

- a slow trend breathing rate pattern. Module 22 interprets as indicative of an approaching or progressing attack an increase vs. baseline, for example, for generally healthy subjects, an attenuation of the typical segmented, monotonic decline of breathing rate typically over at least 1 hour, e.g., over at least 2, 3, or 4 hours, or the transformation of this decline into an increasing breathing rate pattern, depending on the severity of the attack;
- a breathing rate pattern. Module 22 interprets as indicative of an approaching or progressing attack an increase or lack of decrease in breathing rate during the first several hours of sleep, e.g., during the first 2, 3, or 4 hours of sleep.
- a breathing rate variability pattern. Module 22 interprets a decrease in breathing rate variability as indicative of an approaching or progressing attack. Such a decrease generally occurs as the onset of an episode approaches, and intensifies with the progression of shortness of breath during an attack;
- a breathing duty-cycle pattern. Module 22 interprets a substantial increase in the breathing duty-cycle as indicative of an approaching or progressing attack. Breathing duty-cycle patterns include, but are not limited to, inspirium time/total breath cycle time, expirium time/total breath cycle time, and (inspirium+expirium time)/total breath cycle time;
- a change in breathing rate pattern towards the end of night sleep (typically between about 3:00 A.M. and about 6:00 A.M.); and
- interruptions in breathing pattern such as caused by coughs, sleep disturbances, or waking. Module 22 quantifies these events, and determines their relevance to prediction of potential asthma attacks.

Pattern analysis modules 22 and 23 typically determine baseline patterns by analyzing breathing and/or heart rate patterns, respectively, of the subject during non-symptomatic nights. Alternatively or additionally, modules 22 and 23 are programmed with baseline patterns based on population averages. For some applications, such population averages are segmented by characteristic traits such as age, height, weight, and gender.

Reference is again made to FIG. 4, which is a graph illustrating breathing rate patterns of a chronic asthma patient, measured during an experiment conducted in accordance with an embodiment of the present invention. Using techniques described herein, breathing pattern analysis module 22 compares the pattern of line 102 with the baseline pattern of line 100, in order to predict that the patient may experience an asthmatic episode. Module 22 compares the pattern of line 104 with the baseline pattern of line 100 in order to assess a progression of the asthmatic episode.

For some applications of the present invention, the deviation from baseline is defined as the cumulative deviation of the measured pattern from the baseline pattern. A threshold indicative of a clinical condition is set equal to a certain number of standard errors (e.g., one standard error). Alternatively or additionally, other measures of deviation between measured and baseline patterns are used, such as correlation coefficient, mean square error, maximal difference between the patterns, and the area between the patterns. Further alternatively or additionally, pattern analysis module 16 uses a weighted analysis emphasizing specific regions along the patterns, for example, by giving increased weight (e.g., double weight) to an initial portion of sleep (e.g., the first two hours of sleep) or to specific hours, for example as morning approaches (e.g., the hours of 3:00-6:00 a.m.).

Reference is now made to FIGS. 5 and 6, which are graphs of exemplary baseline and measured breathing rate and heart rate nighttime patterns, respectively, and which are generally similar to FIGS. 6 and 7 of U.S. Pat. No. 7,314,451 to Halperin, which is incorporated herein by reference. Lines 200 and 202 (FIGS. 5 and 6, respectively) represent normal baseline patterns in the absence of an asthma attack. The bars represent one standard error. Lines 204 and 206 (FIGS. 5 and 6, respectively) represent patterns during nights prior to an onset of an asthma attack. Detection of the change in pattern between lines 200 and 202 and lines 204 and 206, respectively, enables the early prediction of the approaching asthma attack, or other approaching adverse clinical events.

For some applications of the present invention, pattern analysis module 16 is configured to predict the onset of a clinical manifestation of heart failure, and/or monitor its severity and progression. Module 16 typically determines that an episode is imminent when the module detects increased breathing rate accompanied by increased heart rate, and/or when the monitored breathing and/or heartbeat patterns have specific characteristics that relate to heart failure, such as characteristics that are indicative of apnea, Cheyne-Stokes Respiration (CSR), and/or periodic breathing.

In accordance with the data shown in FIG. 5, for some applications, a subject's respiration is detected on first and second days over similar time durations and at similar time periods (e.g., during the first two, three four, five, or six hours of the subject's sleep). A parameter of the subject's respiration based upon the detected respiration rate on the second day is compared with that of the first day. An alert is generated in response to the comparison indicating that an adverse clinical event is approaching, e.g., in response to determining that the difference between the median, the mean, and/or the maximum respiration rate on the second day and that of the first day exceeds a threshold.

In accordance with the data shown in FIG. 6, for some applications, a subject's heart rate is detected on first and second days over similar time durations and at similar time periods (e.g., during the first two, three, four, five, or six hours of the subject's sleep). A parameter of the subject's cardiac cycle based upon the detected heart rate on the second day is compared with that of the first day. An alert is generated in response to the comparison indicating that an adverse clinical event is approaching, e.g., in response to determining that the difference between the median, the mean, and/or the maximum heart rate on the second day and that of the first day exceeds a threshold.

In accordance with the data shown in FIGS. 5 and 6, for some applications, a subject's respiration rate and heart rate are detected on first and second days over similar time durations and at similar time periods (e.g., during the first two, three four, five, or six hours of the subject's sleep). A parameter of the subject's respiration based upon the detected respiration rate on the second day is compared with that of the first day, and a parameter of the subject's cardiac cycle based upon the detected heart rate on the second day is compared with that of the first day. An alert is generated in response to the comparisons indicating that an adverse clinical event is approaching, e.g., in response to determining that (a) the difference between the median, the mean, and/or the maximum respiration rate on the second day and that of the first day exceeds a threshold, and/or (b) the difference between the median, the mean, and/or the maximum heart rate on the second day and that of the first day exceeds a threshold.

Reference is now made to FIG. 7, which is the same as FIG. 23 of U.S. Pat. No. 7,314,451 to Halperin, which is incorporated herein by reference. FIG. 7 is a graph of baseline and breathing rate nighttime patterns, respectively, measured in accordance with some applications of the present invention. A line 400 represents a normal baseline pattern in the absence of Cheyne-Stokes Respiration, and a line 402 represents a pattern during a night during CSR. The bars represent one standard error. In accordance with the data shown in FIG. 7, for some applications, a subject's respiration is detected on first and second days over similar time durations and at similar time periods (e.g., during the first two, three four, five, or six hours of the subject's sleep). A parameter of the subject's respiration based upon the detected respiration rate on the second day is compared with that of the first day. An alert is generated in response to the comparison indicating that an adverse clinical event is approaching, e.g., in response to determining that the difference between the median, the mean, and/or the maximum respiration rate on the second day and that of the first day exceeds a threshold.

For some applications, techniques described herein are used in conjunction with techniques as are generally described in US 2007/0118054 to Pinhas, which is incorporated herein by reference. For example, as is described with reference to FIG. 18 of US 2007/0118054 to Pinhas, for some applications, system 10 is adapted to monitor multiple clinical parameters such as respiration rate, heart rate, cough occurrence, body movement, deep inspirations, expiration/inspiration ratio, of subject 12. Pattern analysis module 16 is adapted to analyze the respective patterns in order to identify a change in the baseline pattern of the clinical parameters. In some cases, this change, a new baseline that is significantly different from the previous baseline indicates, for example, a change in medication and provides the caregiver or healthcare professional with feedback on the efficacy of treatment.

For some applications, system 10 calculates the average respiration rate and heart rate for predefined time segments. Such time segments can be minutes, hours, or days. By analyzing the history of the patient the system can calculate the correlation of respiration rate and heart rate patterns. When an onset of an asthma attack approaches the correlation of heart rate and respiration rate pattern shows a clear change. For each night the respiration rate and heart rate in sleep during the hours of 11:00 pm to 6:00 am (or over a different time period) is averaged. For each date, a respiration vector of length N with the average respiration rate of the last N nights and a heart rate vector of length N with the average heart rate for the last N nights is defined. N is typically between 3 and 30, for example 10. The correlation coefficient of the heart rate vector and the respiration vector is calculated for each date by system 10. A moving window of several days is used to calculate correlation coefficient changes between the respiration and heart rate vectors. A steady correlation coefficient pattern over at least several days is required to identify a significant change of correlation coefficient from one time interval to another. A significant change is defined as a change in the correlation coefficient level of a magnitude larger than the typical correlation coefficient variation in the previous time interval, e.g., a change larger than 3 standard deviations of the correlation coefficient signal in the previous time interval. System 10 identifies such a significant change as an indication of an approaching clinical event.

As described in US 2007/0118054 to Pinhas, for some applications, during sleep, sleep stage is identified using techniques described therein. In such applications, system uses the identified sleep stages to more effectively monitor a clinical condition of the subject. Control unit 14 analyzes the signal generated by motion sensor 30, and in response thereto, (a) identifies a sleep stage of the subject (e.g., a slow-wave sleep stage, or an REM sleep stage), and (b) identifies a clinical parameter of the subject (e.g., a heart rate or respiratory rate) in the identified sleep stage. The control unit then compares the clinical parameter to a baseline clinical parameter for the identified sleep stage, and generates an output in response thereto.

For example, in some applications, system 10 monitors a subject (e.g., a sleeping child) for fever, e.g., by checking for an elevated heart rate or respiratory rate during slow-wave sleep. By analyzing the signal from motion sensor 30, the control unit identifies that the sleep stage of the subject is indeed a slow-wave sleep stage, and further identifies the heart rate or respiratory rate. The identified heart rate or respiratory rate is then compared to the baseline slow-wave-sleep-stage heart rate or respiratory rate. In response to the comparison, the control unit identifies a likelihood that the subject has fever. If the control unit determines that it is likely that the subject has fever (e.g., in response to the heart rate or respiratory rate being elevated, relative to the baseline), the control unit generates an output (e.g., an alert).

In some applications, the control unit identifies the likelihood that the subject has fever in response to an increasing trend in respiratory rate, e.g., over the course of a night. Using sleep-stage identification as described hereinabove, the control unit discards data acquired during REM sleep of the subject, since respiration rate may increase during REM sleep even in a healthy subject.

In one embodiment, system 10 discards any data while subject 12 showed significant restlessness. Thus for example, the first few minutes the patient is in bed and is still tossing and turning, with his large body movements having significantly stronger signals than the cyclic respiration pattern, are discarded from this analysis. Also, for example, if the sensor signal shows a significant amount of body movement during a particular period of time during the night, the control unit might not identify that the subject likely has fever, even if the heart rate of the subject was elevated during the particular period of time. Since heart rate tends to rise during periods of movement, the control unit does not generate a fever alert, since the elevated heart rate might be a result of the movement, rather than a result of the subject having fever.

Figure 8:
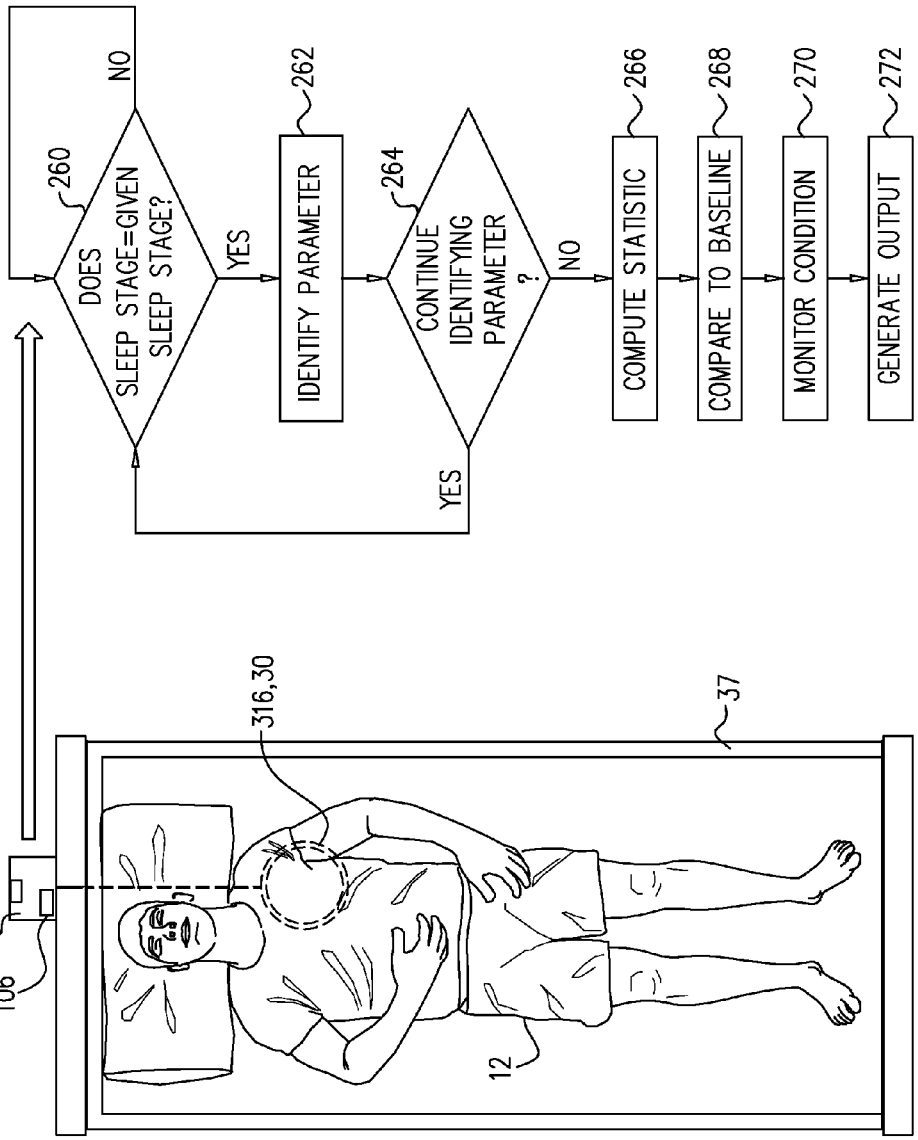
FIG. 8 is a schematic illustration of apparatus for monitoring a subject, in accordance with some applications of the present invention.

Reference is now made to FIG. 8, which is a schematic illustration of apparatus 258 for monitoring a subject 12, in accordance with some applications of the present invention. In particular, apparatus 258 monitors a clinical condition of a subject, in response to a statistic of a clinical parameter (e.g., heart rate or respiratory rate) during a particular sleep stage (e.g., slow-wave sleep). For example, the control unit may (i) identify a sleep stage of the subject, (ii) identify an average of the clinical parameter for the identified sleep stage, and (iii) monitor the clinical condition, by comparing the average to a baseline.

As shown in FIG. 8, a sensor 316 (e.g., motion sensor 30) monitors subject 12, and generates a signal in response thereto. Generally, in the present description, the term "motion sensor 30" is used to refer to a sensor that does not contact or view the subject or clothes the subject is wearing, while the term "sensor 316" or "physiological sensor 316) refers more generally to any type of sensor, e.g., a sensor that includes an electromyographic sensor and/or an imaging sensor. Thus, a phrase such as "sensor 316 (e.g., motion sensor 30)" should be construed to mean that the scope of the described invention includes the use of any type of sensor, but specifically, a non-contact and non-viewing sensor may be used.

At each of a plurality of times (e.g., every two minutes, over a period of ten minutes or more), the control unit analyzes the signal. In response to the analyzing, the control unit ascertains, at an ascertaining step 260, if the sleep stage of the subject is the given sleep stage. If the sleep stage is the given sleep stage, the control unit then identifies, at an identifying step 262, the clinical parameter of the subject. (Steps 260 and 262 are thus part of a "data-gathering" process that is performed by the control unit.) The control unit then decides, at a decision step 264, whether to continue identifying the parameter, i.e., whether more data points should be gathered. If the control unit decides not to continue, the control unit then computes, at a computing step 266, a statistic of the clinical parameter for the given sleep stage over the plurality of times. For example, the control unit may compute the average heart rate that the subject experienced while in slow-wave sleep, over all or a portion of the night.

Following computing step 266, at a comparing step 268, the control unit compares the statistic to a baseline value that is specific to the given sleep stage. For example, the baseline value may be a value of the clinical parameter exhibited during a sleeping session that precedes the present sleeping session, e.g., the subject's average slow-wave-sleep heart rate over a previous night. The control unit then identifies the clinical parameter exhibited during the present sleeping session, as described hereinabove, and compares it to the baseline. Alternatively, the baseline value may be a value of the clinical parameter exhibited at a first time during the present sleeping session, e.g., the heart rate of the subject at the beginning of the night. The control unit then identifies a value of the clinical parameter exhibited at a second time during the sleeping session that follows the first time, e.g., the heart rate of the subject in the middle of the night, and compares the identified value to the baseline. Alternatively, the baseline value may be a typical value for a relevant segment of the general population.

In response to the comparing (e.g., in response to the average slow-wave-sleep heart rate being significantly higher or lower than the baseline), the control unit monitors, at a condition-monitoring step 270, a clinical condition of the subject. In response to the monitoring, the control unit generates an output (e.g., a visual or audio output), at an output-generating step 272.

It is hypothesized by the inventors that averaging the parameter over a specific sleep stage gives a better indication as to the health status of the subject, relative to averaging over the entire night. For example, an average of heart rate over the entire night may reflect the effects of motion or dreams, which may not be relevant to determining the subject's health status. By averaging the heart rate over slow-wave sleep, while ignoring the other sleep stages, these "artifacts" are generally "filtered out".

Typically, the control unit is further configured to compute the baseline value, by executing steps 260, 262, 264, and 266 at an earlier time. In other words, the control unit is configured to gather data, as described hereinabove, during a first plurality of times, and to then establish the baseline value of the parameter by computing (at computing step 266) a first statistic (e.g., average) of the parameter over the first plurality of times. The control unit then gathers data during a second plurality of times, computes a second statistic of the parameter (at computing step 266), and then executes comparing step 268 by comparing the second statistic to the first statistic.

In some applications, the process described above is executed for multiple sleep stages, the data from the multiple sleep stages being used to monitor the clinical condition. That is, for each identified sleep stage, the average respiration rate, heart rate and other clinical parameters are calculated. This data is compared to a baseline defined for that subject for each identified sleep stage, in order to identify the onset or progress of a clinical episode.

For some applications, for each night, for each hour (or for longer durations of time, such as more than two hours) of sleep, counted from the onset of sleep, the average respiration rate, heart rate and other clinical parameters are calculated. This data is compared to baseline (i.e., each of the averages is compared to a respective baseline) in order to identify the onset or progress of a clinical episode.

For some applications, for each night, for each hour (or for longer durations of time, such as more than two hours, as described hereinabove), the average respiration rate, heart rate and other clinical parameters are calculated. This data is compared to baseline in order to identify the onset or progress of a clinical episode. For example, the average respiration rate in sleep during 2:00 AM-3:00 AM is calculated and compared to baseline for that subject in order to identify the onset or progress of a clinical episode.

Figure 9:
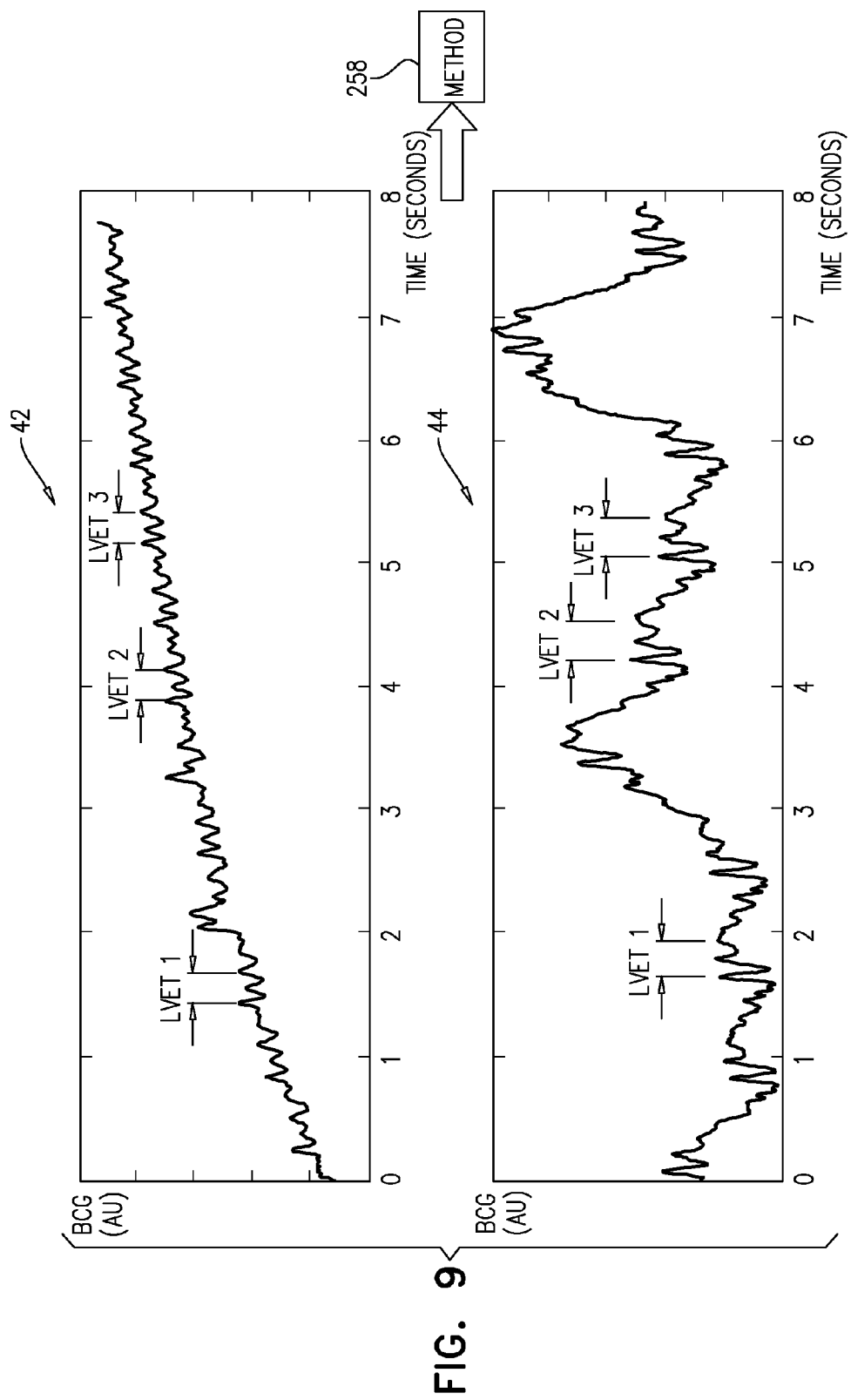
FIGS. 9 and 10 show plots of data obtained from a motion sensor, in accordance with some applications of the present invention.

Reference is now made to FIG. 9, which shows plots of data obtained from motion sensor 30, in accordance with some applications of the present invention. Plot 42 shows the heartbeat-related component of a ballistocardiographic (BCG) signal from sensor 30, in arbitrary units (AU), for a febrile subject, while plot 44 shows the heartbeat-related component of a BCG signal for a healthy subject. (The larger-scale changes in signal strength over the period of time shown in the plots are generally not significant in the context of the description below, in that these changes simply reflect the proximity of the subject to the sensor. For example, the overall upward trend in signal strength in plot 42 simply reflects the fact that the subject moved closer to the sensor over the period of time shown in plot 42, and is not a result of the subject having a fever.)

In some applications, the clinical parameter that is identified by the control unit and compared to the baseline is the left ventricular ejection time (LVET) of the subject.

For example, as shown in plots 42 and 44, the LVET of the subject is lower for a febrile subject than for a healthy subject. In response to identifying that the LVET (or average LVET) of the subject is lower than a baseline, the control unit may identify that it is likely that the subject has fever, and may generate an alert in response thereto. For extracting the heartbeat-related component of the raw sensor signal, and for identifying the LVET, techniques described in (i) US 2014/0371635 to Shinar et al., and/or (ii) Alametsa et al., "Ballistocardiographic studies with acceleration and electromechanical film sensors", Medical Engineering & Physics, 2009, which are incorporated herein by reference, may be used.

Figure 10:
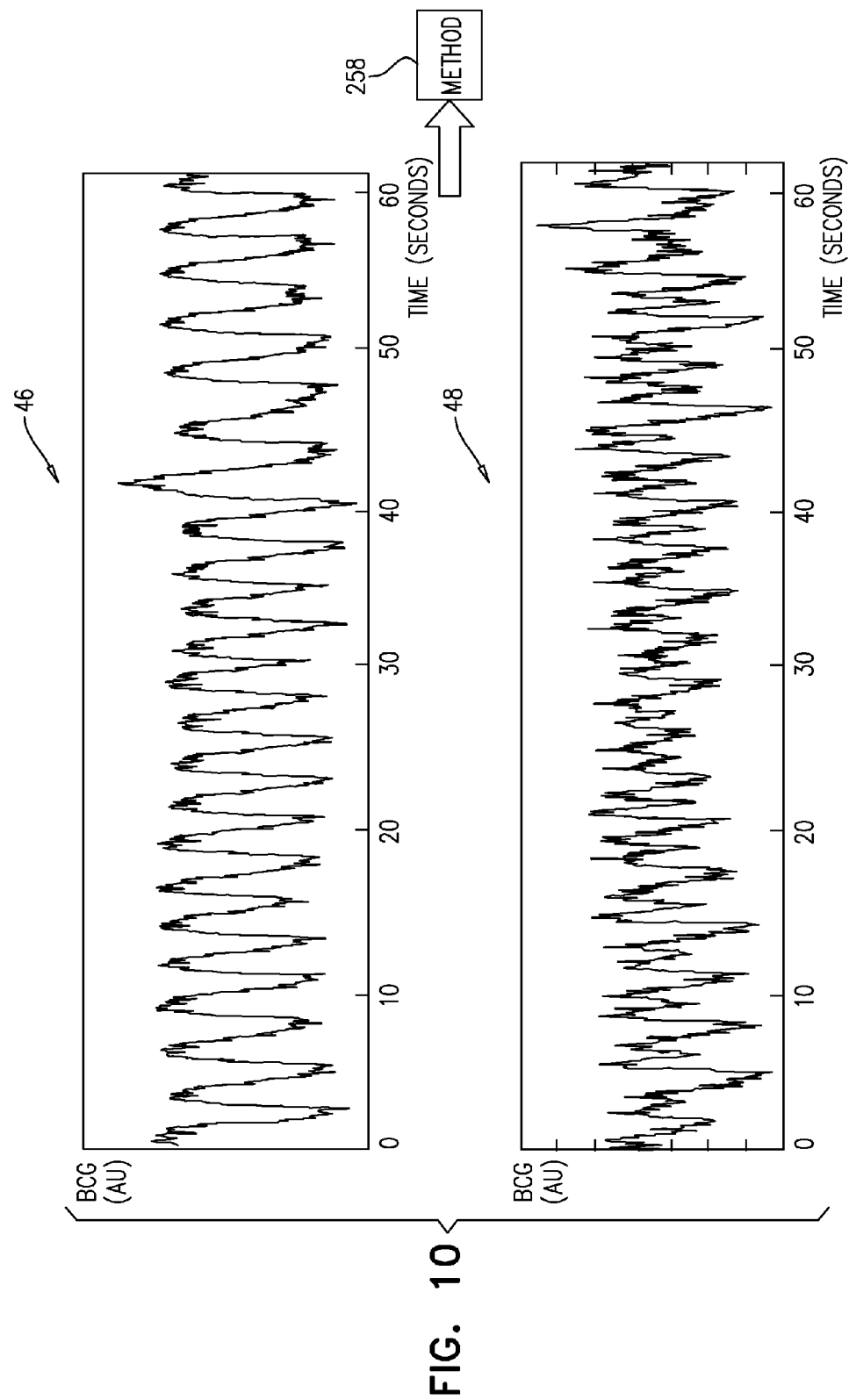

Reference is now made to FIG. 10, which shows plots of data obtained from motion sensor 30, in accordance with some applications of the present invention. Plot 46 shows the respiration-related component of a BCG signal from sensor 30, in arbitrary units, for a healthy subject, while plot 48 shows the respiration-related component of a BCG signal for a febrile subject. The breathing of the febrile subject is labored, as evidenced by the double-peak respiration pattern. In some applications, the control unit identifies the labored breathing, and identifies the likelihood that the subject has fever in response to: (a) comparing the identified clinical parameter to the baseline, as described hereinabove, and (b) identifying the labored breathing.

In some cases, eating within a given amount of time before going to sleep may have a detrimental effect on sleep and/or health of a subject. (For example, the health of a diabetic subject may suffer if the diabetic subject eats within a given amount of time before going to sleep.) In some applications, control unit 14 ascertains, in response to analyzing a signal from a physiological sensor 316 (e.g., motion sensor 30), that the monitored subject ate within a given amount of time before going to sleep. In response to the ascertaining, the control unit generates an output signal (e.g., a visual and/or audio signal) indicative that the subject ate within the given amount of time. For example, the control unit may indicate to the subject, and/or the subject's physician, that the subject should take greater care in the future not to eat so close to bedtime. In some applications, the output signal is communicated to a smartphone of the subject and/or to a smartphone of the subject's physician.

Figure 11:
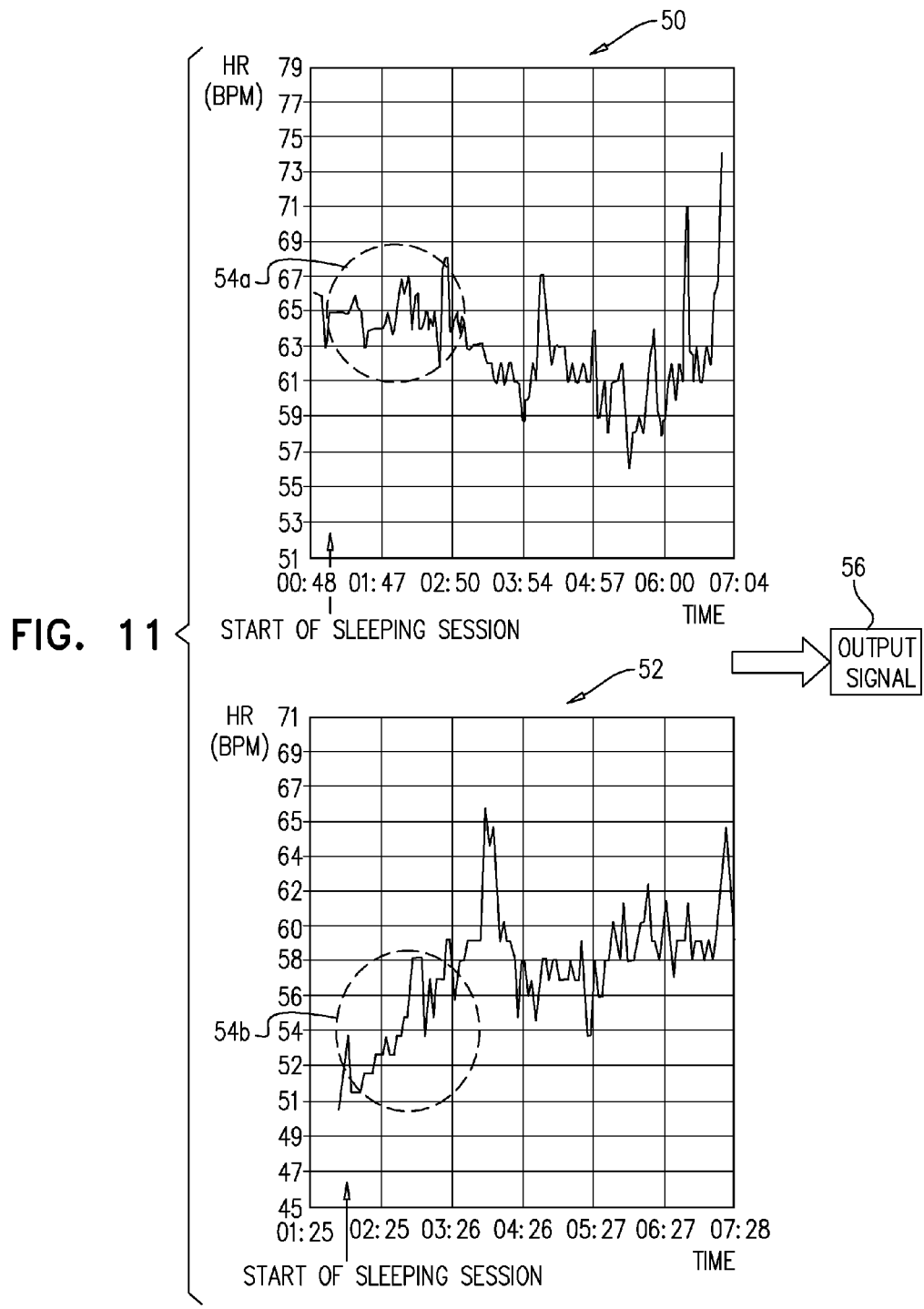
FIG. 11 shows plots of data obtained from a sensor, in accordance with some applications of the present invention.

Reference is now made to FIG. 11, which shows plots of data obtained from sensor 316, in accordance with some applications of the present invention. Plot 50 shows the heart-rate signal of a subject during a sleeping session, after the subject ate within three hours of the start of the sleeping session. Plot 52 shows the heart-rate signal of the same subject during a different sleeping session, after the subject did not eat within six hours of the start of the sleeping session. For each plot, control unit 14 identified, in response to analyzing the heart-rate signal, a likelihood that the subject ate within a given amount of time of going to sleep, and generated an output signal 56 in response thereto. That is, (i) for plot 50, the control unit generated an output indicative that the subject likely ate within three hours of going to sleep, and (ii) for plot 52, the control unit generated an output indicative that the subject likely did not eat within six hours of going to sleep.

Typically, the control unit identifies the likelihood that the subject ate shortly before going to sleep by analyzing a portion of the heart-rate signal that is near the beginning of the sleeping session. This portion is marked as portion 54a in plot 50, and as portion 54b in plot 52. Portions 54a and 54b differ from one another as follows:

(a) In portion 54a, the heart rate (HR) of the subject is elevated, relative to portion 54b. The inventors hypothesize that the elevated heart rate is due to the additional activity of the gastrointestinal tract in digesting the food that was consumed shortly before the start of the sleeping session.

(b) In portion 54a, the heart rate of the subject is generally non-increasing, whereas in portion 54b, the heart rate is increasing. The inventors hypothesize that the increasing heart rate in portion 54b is driven by the sympathetic nervous system, which tends to become more active as the sleeping session progresses. In portion 54a, on the other hand, the level of gastrointestinal activity of the subject, which is relatively high at the beginning of the sleeping session, decreases as the sleeping session progresses. This decrease in gastrointestinal activity, which has the effect of lowering the heart rate of the subject, counteracts the increase in sympathetic nervous activity with respect to heart rate; thus, the heart rate of the subject remains generally constant.

In response to at least one of the differences above, the control unit may identify the likelihood that the subject ate shortly before going to sleep. For example:

(a) The control unit may identify a relatively high likelihood that the subject ate, by determining that the heart rate is greater than a baseline heart rate. (The baseline is typically subject-specific, and is typically learned by the control unit.) For example, the heart rate of around 65 beats per minute (BPM) in portion 54a is greater than 52-58 BPM, which, from portion 54b, appears to be a reasonable baseline heart rate for the subject.

(b) Alternatively or additionally, the control unit may identify a relatively high likelihood that the subject ate, by determining that the heart rate of the subject does not increase over a particular interval by more than a threshold.

In one embodiment, pattern analysis module 16 is adapted to identify preterm labor in a pregnant woman. Preterm labor is the leading cause of perinatal morbidity and mortality in the United States. Early diagnosis of preterm labor enables effective tocolytic therapy to prevent full labor. In one embodiment, system 10 is adapted to identify the mechanical signal of contractions. In one embodiment, motion sensor 30 is adapted to include multiple sensors located in the vicinity of the legs, pelvis, lower abdomen, and upper abdomen. Pattern analysis module 16 identifies a mechanical signal that is strongest in the area of the lower abdomen and pelvis and weaker in the upper abdomen as a signal indicative of contractions. In one embodiment, system 10 is adapted to differentiate between Braxton Hicks contractions and normal contractions in order to minimize false alarms of preterm labor. In one embodiment, differentiation between regular contractions and Braxton Hicks contractions is done by comparing the frequency and strength of the contractions. In one embodiment, the strength of the contraction mechanical signal is normalized by the strength of the rhythmic heart and respiration signals. In one embodiment, the system logs the contractions and alerts the subject or a clinician upon having the number or hourly rate of contractions exceed a predefined threshold.

Normal breathing patterns in sleep are likely to be subject to slow changes over days, weeks, months and years. Some changes are periodic due to periodic environmental changes like change in seasons, or to a periodic schedule such as a weekly schedule (for example outdoor play every Saturday), or biological cycles such as the menstrual cycle. Other changes might be monotonically progressive—for example, changes due to children growing up or adults aging. It is desirable to track these slow changes dynamically via an adaptive system.

In an embodiment of the present invention, system 10 is adapted to monitor parameters of the patient including breathing rate, heart rate, coughing counts, expiration/inspiration ratios, augmented breaths, deep inspirations, tremor, sleep cycle, and restlessness patterns, among other parameters. These parameters are defined herein as "clinical parameters."

In an embodiment of the present invention, pattern analysis module 16 combines clinical parameter data generated from one or more of analysis modules 22, 23, 26, 28, 29, and analyzes the data in order to predict and/or monitor a clinical event. For some applications, pattern analysis module 16 derives a score for each parameter based on the parameter's deviation from baseline values (either for the specific patient or based on population averages). Pattern analysis module 16 may combine the scores, such as by taking an average, maximum, standard deviation, or other function of the scores. The combined score is compared to one or more threshold values (which may be predetermined) to determine whether an episode is predicted, currently occurring, or neither predicted nor occurring, and/or to monitor the severity and progression of an occurring episode. For some applications, pattern analysis module 16 learns the criteria and/or functions for combining the individual parameter scores for the specific patient or patient group based on personal history. For example, pattern analysis module 16 may perform such learning by analyzing parameters measured prior to previous clinical events.

In one aspect, pattern analysis module 16 is adapted to analyze the respective patterns, for example, the patterns of slow changes mentioned above, in order to identify a change in baseline characteristic of the clinical parameters. For example, in order to identify the slow change in average respiration rate in sleep for a child due to growing up, a monthly average of the respiration rate in sleep is calculated. System 10 then calculates the rate of change in average respiration rate from one month to the next and displays that to the patient or healthcare professional.

In some applications, the control unit identifies a baseline value corresponding to a day of the week, and derives a score based on a deviation of the identified clinical parameter from the day-specific baseline value. For example, as noted above, breathing patterns in sleep may change over a weekly schedule of the subject; for example, physical activity of the subject may generally recur on a particular day of the week. The control unit identifies the baseline value in response to the weekly schedule. For example, in response to recurring outdoor play on a particular day of the week, the control unit may identify a breathing-rate baseline value corresponding to the particular day of the week that is greater than the baseline value for other days of the week. (It is noted that a baseline value may be said to correspond to a particular day of the week if it corresponds to the sleeping period at the end of, or immediately following, the particular day of the week. For example, the baseline value identified for a subject who went to sleep at 1:00 a.m. Monday would typically be the baseline value that corresponds to Sunday.) Additionally or alternatively, system 10 identifies a first baseline value corresponding to a weekend day, and a second baseline value, which is different from the first baseline value, corresponding to a weekday. For example, system 10 may identify that the average respiration rate in sleep during weekends is higher than on weekdays, and may therefore use in weekends a different (i.e., higher) baseline for comparison and decision on whether a clinical episode is present or oncoming.

As noted above, in some applications, the baseline value is identified in response to environmental changes. For example, as noted above, the baseline value may be identified in response to a change in seasons. Alternatively or additionally, the baseline value may be identified in response to changes in room-environment parameters, such as room temperature and humidity. In some applications, system 10 comprises a temperature sensor 106 (FIG. 8) configured to detect a room temperature and/or an in-bed temperature (i.e., the temperature of the "microclimate" underneath the subject's sheets), and the baseline value is identified in response to the room temperature and/or in-bed temperature. For example, the control unit may identify a higher heart-rate baseline value for a higher room temperature and/or a higher in-bed temperature, relative to a lower room temperature and/or a lower in-bed temperature, since the heart rate of the subject is expected to increase with an increase in ambient temperature.

In one embodiment, system 10 monitors and logs the clinical condition of a patient over an extended period of time. During the same period of time, behavioral patterns, treatment practices and external parameters that may be affecting the patient's condition are monitored and logged as well. This information is input into system 10. System 10 calculates a score for the clinical condition of the patient based on the measured clinical parameters.

In general, control unit 14 may be embodied as a single control unit 14, or a cooperatively networked or clustered set of control units. Control unit 14 is typically a programmed digital computing device comprising a central processing unit (CPU), random access memory (RAM), non-volatile secondary storage, such as a hard drive or CD ROM drive, network interfaces, and/or peripheral devices. Program code, including software programs, and data are loaded into the RAM for execution and processing by the CPU and results are generated for display, output, transmittal, or storage, as is known in the art. Typically, control unit 14 is connected to one or more sensors via one or more wired or wireless connections. Control unit 14 is typically configured to receive signals (e.g., motions signals) from the one or more sensors, and to process these signals as described herein. In the context of the claims and specification of the present application, the term "motion signal" is used to denote any signal that is generated by a sensor, upon the sensor sensing motion. Such motion may include, for example, respiratory motion, cardiac motion, or other body motion, e.g., large body-movement. Similarly, the term "motion sensor" is used to denote any sensor that senses motion, including the types of motion delineated above.

Techniques described herein may be practiced in combination with techniques described in one or more of the following patents and patent applications, which are incorporated herein by reference. In some applications, techniques and apparatus described in one or more of the following applications are combined with techniques and apparatus described herein:

U.S. patent application Ser. No. 11/048,100, filed Jan. 31, 2005, which issued as U.S. Pat. No. 7,077,810;

U.S. patent application Ser. No. 11/197,786, filed Aug. 3, 2005, which issued as U.S. Pat. No. 7,314,451;

U.S. patent application Ser. No. 11/446,281, filed Jun. 2, 2006, which issued as U.S. Pat. No. 8,376,954;

U.S. patent application Ser. No. 11/552,872, filed Oct. 25, 2006, now abandoned, which published as US 2007/0118054;

U.S. patent application Ser. No. 11/755,066, filed May 30, 2007, now abandoned, which published as US 2008/0114260;

U.S. patent application Ser. No. 11/782,750, filed Jul. 25, 2007, which issued as U.S. Pat. No. 8,403,865;

U.S. patent application Ser. No. 12/113,680, filed May 1, 2008, which published as US 2008/0275349;

U.S. patent application Ser. No. 12/842,634, filed Jul. 23, 2010, which issued as U.S. Pat. No. 8,517,953;

U.S. patent application Ser. No. 12/938,421, filed Nov. 3, 2010, which issued as U.S. Pat. No. 8,585,607;

U.S. patent application Ser. No. 12/991,749, filed Nov. 9, 2010, which issued as U.S. Pat. No. 8,821,418;

U.S. patent application Ser. No. 13/107,772, filed May 13, 2011, which issued as U.S. Pat. No. 8,491,492;

U.S. patent application Ser. No. 13/305,618, filed Nov. 28, 2011, which published as US 2012/0132211;

U.S. patent application Ser. No. 13/389,200, filed Jun. 13, 2012, now abandoned, which published as US 2012/0253142;

U.S. patent application Ser. No. 13/750,957, filed Jan. 25, 2013, which issued as U.S. Pat. No. 8,603,010

U.S. patent application Ser. No. 13/750,962, filed Jan. 25, 2013, which issued as U.S. Pat. No. 8,679,034;

U.S. patent application Ser. No. 13/863,293, filed Mar. 15, 2013, now abandoned, which published as US 2013/0245502;

U.S. patent application Ser. No. 13/906,325, filed May 30, 2013, which issued as U.S. Pat. No. 8,882,684;

U.S. patent application Ser. No. 13/921,915, filed Jun. 19, 2013, which issued as U.S. Pat. No. 8,679,030;

U.S. patent application Ser. No. 14/019,371, filed Sep. 5, 2013, which published as US 2014/0005502;
U.S. patent application Ser. No. 14/020,574, filed Sep. 6, 2013, which issued as U.S. Pat. No. 8,731,646;
U.S. patent application Ser. No. 14/054,280, filed Oct. 15, 2013, which issued as U.S. Pat. No. 8,734,360;
U.S. patent application Ser. No. 14/150,115, filed Jan. 8, 2014, which issued as U.S. Pat. No. 8,840,564;
U.S. patent application Ser. No. 14/231,855, filed Apr. 1, 2014, which published as US 2014/0207204;
U.S. patent application Ser. No. 14/454,300, filed Aug. 7, 2014, which issued as U.S. Pat. No. 8,942,779;
U.S. patent application Ser. No. 14/458,399, filed Aug. 13, 2014, which published as US 2014/0350351;
U.S. patent application Ser. No. 14/474,357, filed Sep. 2, 2014, which published as US 2014/0371635; International Patent Application PCT/IL2005/000113, which published as WO 2005/074361;
International Patent Application PCT/IL2006/000727, which published as WO 2006/137067;
International Patent Application PCT/IB2006/002998, which published as WO 2007/052108;
International Patent Application PCT/IL2008/000601, which published as WO 2008/135985;
International Patent Application PCT/IL2009/000473, which published as WO 2009/138976;
International Patent Application PCT/IL2011/050045, which published as WO 2012/077113;
International Patent Application PCT/IL2013/050283, which published as WO 2013/150523; and
International Patent Application PCT/IL2014/050644, which published as WO 2015/008285.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for monitoring a subject, the apparatus comprising:
a sensor, configured to monitor the subject and to generate a signal in response thereto; and
a control unit, configured to:
analyze the signal,
in response to the analyzing, identify a clinical parameter of the subject,
receive an indication of an environmental change,
taking into account the environmental change:
identify a baseline value for the clinical parameter,
compare the identified clinical parameter to the baseline value, and
in response to the comparing, perform an action selected from the group consisting of: determine whether a clinical episode is predicted, determine whether a clinical episode is currently occurring, and monitor an occurring clinical episode, and
generate an output in response thereto.

2. The apparatus according to claim 1, wherein the control unit is configured to:
identify the baseline value of the clinical parameter in response to the environmental change,
derive a score based upon a deviation of the identified clinical parameter from the baseline value, and
perform the selected action in response to the score.

3. The apparatus according to claim 2, wherein the control unit is configured to identify the baseline value in response to a change in seasons.

4. Apparatus for monitoring a subject, the apparatus comprising:
a sensor, configured to monitor the subject and to generate a signal in response thereto; and
a control unit, configured to:
analyze the signal,
in response to the analyzing, identify a clinical parameter of the subject,
receive an indication of a day of the week,
taking into account the day of the week:
identify a baseline value for the clinical parameter,
compare the identified clinical parameter to the baseline value,
in response to the comparing, perform an action selected from the group consisting of: determine whether a clinical episode is predicted, determine whether a clinical episode is currently occurring, and monitor an occurring clinical episode, and
generate an output in response thereto.

5. The apparatus according to claim 4, wherein the control unit is configured to:
identify the baseline value of the clinical parameter by identifying a baseline value for the clinical parameter that corresponds to the day of the week,
derive a score based upon a deviation of the identified clinical parameter from the baseline value, and
perform the selected action in response to the score.

6. The apparatus according to claim 5, wherein the control unit is configured to identify the baseline value in response to a weekly schedule of the subject.

7. The apparatus according to claim 6, wherein the control unit is configured to identify the baseline value in response to physical activity of the subject generally recurring on a particular day of the week.

8. The apparatus according to claim 5, wherein the control unit is configured to identify a first baseline value corresponding to a weekend day, and a second baseline value, which is different from the first baseline value, corresponding to a weekday.

9. The apparatus according to claim 8, wherein the clinical parameter is a respiration rate of the subject, and wherein the control unit is configured to identify a higher baseline value for a weekend day than for a weekday.

10. Apparatus for monitoring a subject, the apparatus comprising:
a sensor, configured to monitor the subject and to generate a signal in response thereto; and
a control unit, configured to:
analyze the signal,
in response to the analyzing, identify a clinical parameter of the subject,
receive an indication of a menstrual cycle of the subject,
taking into account the menstrual cycle of the subject:
identify a baseline value of the clinical parameter,
compare the identified clinical parameter to the baseline value, and
in response to the comparing, perform an action selected from the group consisting of: determine whether a clinical episode is predicted, determine whether a clinical episode is currently occurring, and monitor an occurring clinical episode, and
generate an output in response thereto.

11. The apparatus according to claim 10, wherein the control unit is configured to:

identify the baseline value of the clinical parameter in response to the subject's menstrual cycle, derive a score based upon a deviation of the identified clinical parameter from the baseline value, and perform the selected action in response to the score.

12. Apparatus for monitoring a subject, the apparatus comprising:

a sensor, configured to monitor the subject during a sleeping session of the subject, and to generate a signal in response thereto; and a control unit, configured to:

analyze the sensor signal, and in response to an aspect of the sensor signal starting from a given time period after a beginning of the sleeping session, perform an action selected from the group consisting of: determine whether a clinical episode is predicted, determine whether a clinical episode is currently occurring, and monitor an occurring clinical episode, and generate an output in response thereto.

* * * * *